(12) United States Patent  (10) Patent No.: US 8,039,481 B2
Schudok et al.  (45) Date of Patent: Oct. 18, 2011

(54) TETRAHYDROFURAN DERIVATIVES FOR USE AS INHIBITORS OF MATRIX METALLOPROTEINASES

(75) Inventors: Manfred Schudok, Eppstein (DE); Hans Matter, Langenselbold (DE); Armin Hofmeister, Dexheim (DE)

(73) Assignee: Sanofi-Aventis, Paris (FR)

( * ) Notice: Subject to any disclaimer, the term of this patent is extended or adjusted under 35 U.S.C. 154(b) by 989 days.

(21) Appl. No.: 11/777,324

(22) Filed: Jul. 13, 2007

(65) Prior Publication Data

US 2008/0039489 A1   Feb. 14, 2008

Related U.S. Application Data

(63) Continuation of application No. PCT/EP2006/000047, filed on Jan. 5, 2006.

(30) Foreign Application Priority Data

Jan. 19, 2005 (DE) .................. 10 2005 002 500

(51) Int. Cl.
*A61K 31/4355* (2006.01)
*C07D 471/04* (2006.01)
(52) U.S. Cl. ...................................... 514/302; 546/115
(58) Field of Classification Search ............. 546/115; 514/302
See application file for complete search history.

(56) References Cited

U.S. PATENT DOCUMENTS

| | | |
|---|---|---|
| 5,866,587 A | 2/1999 | de Nanteuil et al. |
| 6,207,672 B1 | 3/2001 | Thorwart |
| 6,339,092 B1 | 1/2002 | de Nanteuil et al. |
| 6,573,277 B2 | 6/2003 | Thorwart |
| 6,770,647 B2 | 8/2004 | Sheppeck et al. |
| 6,815,440 B2 | 11/2004 | Thorwart |
| 7,205,315 B2 | 4/2007 | Schudok |
| 2002/0137744 A1 | 9/2002 | de Nanteuil et al. |
| 2007/0155778 A1 | 7/2007 | Schudok |

FOREIGN PATENT DOCUMENTS

| | | |
|---|---|---|
| WO | WO 99/06410 | 2/1999 |
| WO | 03/016248 A2 | 2/2003 |
| WO | 2005/030728 A1 | 4/2005 |
| WO | 2006/002764 | 1/2006 |

*Primary Examiner* — Patricia Morris

(74) *Attorney, Agent, or Firm* — James W. Bolcsak; Scully, Scott, Murphy & Presser, P.C.

(57) ABSTRACT

The present invention includes novel derivatives of bicyclic tetrahydrofuran imino acids of formula I,

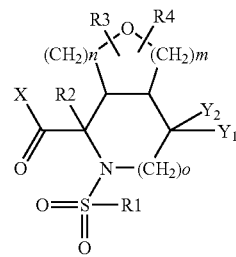

processes for their preparation, and uses thereof as medicaments. The compounds are suitable for use in the therapy and prophylaxis of diseases which are associated with an increased matrix metalloproteinase activity.

2 Claims, No Drawings

TETRAHYDROFURAN DERIVATIVES FOR USE AS INHIBITORS OF MATRIX METALLOPROTEINASES

The invention relates to novel derivatives of bicyclic tetrahydrofuran imino acids, process for their preparation, and use thereof as medicaments.

In diseases such as osteoarthritis and rheumatism there is destruction of the joint caused in particular by the proteolytic breakdown of collagen by collagenases. Collagenases belong to the superfamily of metalloproteinases (MP) or matrix metalloproteinases (MMPs). The MMPs form a group of Zn-dependent enzymes involved in the biodegradation of the extracellular matrix (D. Yip et al., Investigational New Drugs 1999, 17, 387-399 and Michaelides et al., Current Pharmaceutical Design 1999, 5, 787-819). These MMPs are capable in particular of breaking down fibrillary and non-fibrillary collagen, and proteoglycans, both of which represent important matrix constituents. MMPs are involved in processes of wound healing, of tumor invasion, metastasis migration and in angiogenesis, multiple sclerosis and heart failure (Michaelides et al., page 788; see above). In particular they play an important part in the breakdown of the joint matrix in arthrosis and arthritis, whether osteoarthrosis, osteoarthritis or rheumatoid arthritis.

The activity of MMPs is moreover essential for many of the processes involved in atherosclerotic plaque formation, such as infiltration of inflammatory cells, smooth muscle cell migration, and proliferation and angiogenesis (S. J. George, Exp. Opin. Invest. Drugs 2000, 9 (5), 993-1007). Moreover, matrix degradation by MMPs may cause plaque instabilities or even ruptures, possibly leading to the signs and symptoms of atherosclerosis, unstable angina pectoris, myocardial infarction or stroke (E. J. M. Creemers et al, Circulation Res. 2001, 89, 201-210). Considered overall, the entire MMP family can break down all the components of the extracellular matrix of the blood vessels; their activity is therefore subject in a high degree to regulatory mechanisms in normal blood vessels. Elevated MMP activity during plaque formation and plaque instability is caused by increased cytokine- and growth factor-stimulated gene transcription, increased zymogen activation and an imbalance in the MMP-TIMP ratio (tissue inhibitors of metalloproteases). It thus appears plausible that MMP inhibition or restoration of the MMP-TIMP balance will be of assistance in the treatment of atherosclerotic disorders. In addition, it is becoming increasingly clear that besides atherosclerosis, other cardiovascular disorders are also at least partly caused by an elevated MMP activity, such as, for example, restenosis, dilated cardiomyopathy and the myocardial infarction which has already been mentioned. It has been possible to show in experimental animal models of these disorders that distinct improvements can be achieved by administration of synthetic inhibitors, e.g. relating to the formation of atherosclerotic lesions, neointima formation, left ventricular remodeling, dysfunction of pumping efficiency or healing of infarctions. Detailed tissue analysis in various preclinical studies with MMP inhibitors showed reduced collagen damage, improved extracellular matrix remodeling and an improved structure and function of myocardium and vessels. Of these processes, in particular matrix remodeling processes and MMP-regulated fibroses are regarded as important components in the progression of heart diseases (infarction) (Drugs 2001, 61, 1239-1252).

MMPs cleave matrix proteins such as collagen, laminin, proteoglycans, elastin or gelatin, and MMPs moreover process (i.e. activate or deactivate) by cleavage a large number of other proteins and enzymes under physiological conditions, so that they are important in the whole body, with particular importance in connective tissue and bone.

A large number of different MMP inhibitors are known (EP 0 606 046; WO 94/28889; WO 96/27583; or else reviews such as Current Medicinal Chemistry 8, 425-74 (2001), Current Medicinal Chemistry 11, 2911-2977 (2004) or Current Opinion in Drug Discovery & Development 7, 513-535 (2004). It has emerged from initial clinical studies on humans that MMPs cause side effects. The side effects which are chiefly mentioned are musculoskeletal pain or arthralgias. It is unambiguous from the prior art that selective inhibitors will be able to reduce these side effects mentioned (Yip, page 387, see above). Specificity in relation to MMP-1 should be particularly emphasized in this connection, because these unwanted side effects evidently occur to an increased extent with inhibition of MMP-1.

A disadvantage of known MMP inhibitors is therefore frequently the lack of specificity. Most MMP inhibitors inhibit many MMPs simultaneously because of the similarity in structure of the catalytic domain of the MMPs. Accordingly, the inhibitors act in an unwanted way on the enzymes, including those with a vital function (Massova I, et al., The FASEB Journal (1998) 12, 1075-1095).

Considered structurally, most matrix metalloproteinase inhibitors can be divided into sulfonamides and sulfones carrying a zinc-binding group. Particular preference is given in this connection to the carboxylic acid group and very particularly to the hydroxamic acid group. The properties are described in detain for instance in the review articles cited above. The group of sulfonamides is characterized in that an amino carboxylic acid or imino carboxylic acid basic structure is often utilized as structural basis. Bicyclic imino acid basic structures are also employed, especially in combination with phenylic ring systems. By contrast, to date only comparatively few heterobicyclic imino acid basic structures are to be found in MMP inhibitors, especially when oxygen-containing heteroaryls, i.e. furans, are considered. These bicyclic furan systems have been described for example in EP 0803505, EP 1065209, EP 1217002 or in WO 99/06410 and are also disclosed in similar form in PCT/US02/26018.

In the effort to find effective compounds for the treatment of connective tissue disorders, it has now been found that the derivatives employed according to the invention are strong inhibitors of matrix metalloproteinases MMP-2, MMP-3 MMP-8, MMP-9 and MMP-13, but at the same time there is considerably less inhibition of MMP-1 which is possibly responsible for the side effects.

The invention therefore relates to a compound of the formula I

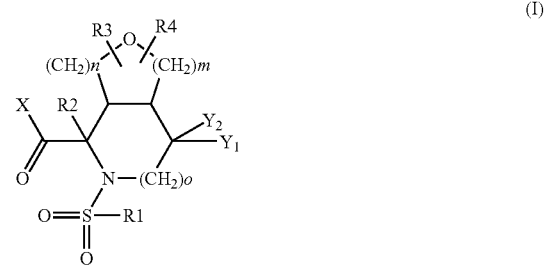

and/or all stereoisomeric forms of the compound of the formula I and/or mixtures of these forms in any ratio, and/or a physiologically tolerated salt of the compound of the formula I, where
R1 is A-ring1-B-ring2-D-ring3-E-ring4

A is —($C_0$-$C_4$)-alkylene,
B, D and E are identical or different and are independently of one another —($C_0$-$C_4$)-alkylene or the radical

-B1-B2-B3- in which
B1 is —$(CH_2)_v$— in which v is the integer zero, 1 or 2,
B3 is —$(CH_2)_w$— in which w is the integer zero, 1 or 2,
with the proviso that the total of v and w amounts to zero, 1 or 2, and
B2 is
 1) —C(O)—
 2) —($C_2$-$C_4$)-alkenylene,
 3) —$S(O)_x$— where x is the integers zero, 1 or 2,
 4) —N(R6)- in which R6 is hydrogen atom, methyl or ethyl,
 5) —N(R6)-C(Y)— in which Y is oxygen atom or sulfur atom, and R6 is as defined above,
 6) —C(Y)—N(R6)- in which Y is oxygen atom or sulfur atom, and R6 is as defined above,
 7) —N(R6)-$SO_2$— in which R6 is as defined above,
 8) —$SO_2$—N(R6)- in which R6 is as defined above,
 9) —N(R6)-$SO_2$—N(R6)- in which R6 is as defined above,
 10) —N(R6)-C(Y)—N(R6)- in which Y is oxygen atom or sulfur atom, and R6 is as defined above,
 11) —O—C(O)—N(R6)-,
 12) —NH—C(O)—O—,
 13) —O—,
 14) —C(O)—O—,
 15) —O—C(O)—,
 16) —O—C(O)—O—,
 17) —O—$CH_2$—C(O)—,
 18) —O—$CH_2$—C(O)—O—,
 19) —O—$CH_2$—C(O)—N(R6)- in which R6 is as defined above,
 20) —C(O)—$CH_2$—O—,
 21) —O—C(O)—$CH_2$—O—,
 22) —N(R6)-C(O)—$CH_2$—O— in which R6 is as defined above,
 23) —O—$(CH_2)_s$—O— in which s is the integer 2 or 3, or
 24) —O—$(CH_2)_t$—N(R6)- in which t is the integer 2 or 3, and R6 is as defined above,
 25) —N(R6)-$(CH_2)_u$—O— in which u is the integer 2 or 3 and R6 is as defined above,
 26) —N(R6)-N(R6)- in which R6 is as defined above,
 27) —N=N—,
 28) —N(R6)-CH=N— in which R6 is as defined above,
 29) —N=CH—N(R6)- in which R6 is as defined above,
 30) —N(R6)-C(R7)=N— in which R6 is as defined above, and R7 is —NH—R6,
 31) —N=C(R7)-N(R6)- in which R6 is as defined above, and R7 is —NH—R6, or
 32) —($C_2$-$C_6$)-alkynylene,
ring1, ring2 or ring3 are identical or different and is independently of one another
 1) covalent bond,
 2) —($C_6$-$C_{14}$)-aryl in which aryl is unsubstituted or substituted independently of one another once, twice or three times by G, or
 3) 4- to 15-membered Het ring in which Het ring is unsubstituted or substituted independently of one another once, twice or three times by G,
ring4 is
 1) —($C_6$-$C_{14}$)-aryl in which aryl is unsubstituted or substituted independently of one another once, twice or three times by G,
 2) 4- to 15-membered Het ring in which the Het ring is unsubstituted or substituted independently of one another once, twice or three times by G, or
 3) is one of the following radicals

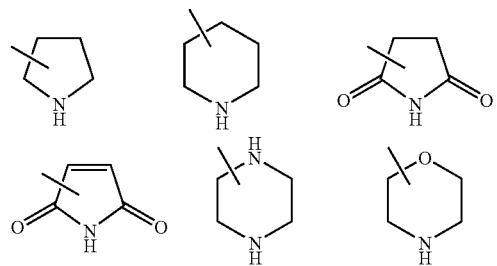

and these radicals are unsubstituted or substituted independently of one another once, twice or three times by G,
G is
 1) hydrogen atom,
 2) halogen,
 3) =O,
 4) —($C_1$-$C_6$)-alkyl in which alkyl is unsubstituted or substituted once, twice or three times by halogen, —($C_3$-$C_6$)-cycloalkyl, —($C_2$-$C_6$)-alkynyl, —($C_6$-$C_{14}$)-aryl or Het ring,
 5) —($C_6$-$C_{14}$)-aryl,
 6) Het ring,
 7) —C(O)—O—R10 in which R10 is
  a) —($C_1$-$C_6$)-alkyl in which alkyl is unsubstituted or substituted once or twice by —($C_3$-$C_6$)-cycloalkyl, —($C_2$-$C_6$)-alkynyl, —($C_6$-$C_{14}$)-aryl, or Het ring,
  b) —($C_6$-$C_{14}$)-aryl or
  c) Het ring,
 8) —C(S)—O—R10 in which R10 is as defined above,
 9) —C(O)—NH—R11 in which R11 is
  a) —($C_1$-$C_6$)-alkyl in which alkyl is unsubstituted or substituted once or twice by —($C_3$-$C_6$)-cycloalkyl, —($C_2$-$C_6$)-alkynyl, —($C_6$-$C_{14}$)-aryl or Het ring, or
  b) —($C_6$-$C_{14}$)-aryl or
  c) Het ring,
 10) is —C(S)—NH—R11 in which R11 is as defined above,
 11) —O—R12 in which R12 is
  a) hydrogen atom,
  b) —($C_1$-$C_6$)-alkyl in which alkyl is unsubstituted or substituted once, twice or three times by halogen, —($C_3$-$C_6$)-cycloalkyl, —($C_2$-$C_6$)-alkynyl, —($C_6$-$C_{14}$)-aryl or Het ring,
  c) —($C_6$-$C_{14}$)-aryl,
  d) Het ring,
  e) —C(O)—O—R13 in which R13 is
   e1) —($C_1$-$C_6$)-alkyl in which alkyl is unsubstituted or substituted once or twice by —($C_3$-$C_6$)-cycloalkyl, —($C_2$-$C_6$)-alkynyl, —($C_6$-$C_{14}$)-aryl, or Het ring, or
   e2) —($C_6$-$C_{14}$)-aryl or
   e3) Het ring, f) —C(S)—O—R13 in which R13 is as defined above,
g) —C(O)—NH—R14 in which R14 is
  g)1) —($C_1$-$C_6$)-alkyl in which alkyl is unsubstituted or substituted once or twice by —($C_3$-$C_6$)-cycloalkyl, —($C_2$-$C_6$)-alkynyl, —($C_6$-$C_{14}$)-aryl or Het ring, or
  g)2) —($C_6$-$C_{14}$)-aryl or
  g)3) Het ring, or
h) —C(S)—NH—R14 in which R14 is as defined above,
12) —C(O)—R10 in which R10 is as defined above,
13) —S(O)$_p$—R12 in which R12 is as defined above, and p is the integers zero, 1 or 2,
14) —$NO_2$,
15) —CN or
16) —N(R15)-R12 in which R15 is
  a) hydrogen atom,
  b) —($C_1$-$C_6$)-alkyl or
  c) —$SO_2$—($C_1$-$C_6$)-alkyl in which alkyl is unsubstituted or substituted once or twice by —($C_3$-$C_6$)-cycloalkyl, —($C_2$-$C_6$)-alkynyl, —($C_6$-$C_{14}$)-aryl or Het ring, and R12 is as defined above, or
17) —$SO_2$—N(R12)-R16 in which R12 is as defined above, and R16 is as defined below,
X is —OH or —NH—OH,
m is the integer zero, 1 or 2,
n is the integer zero, 1 or 2 and with the proviso that the total of m and n amounts to 2,
o is the integer 1 or 2,
Y1 and Y2 are identical or different and are independently of one another
  1) hydrogen atom,
  2) halogen,
  3) —CN,
  4) —($C_1$-$C_6$)-alkyl in which alkyl is unsubstituted or substituted once, twice or three times by halogen, —($C_3$-$C_6$)-cycloalkyl, —($C_2$-$C_6$)-alkynyl, —($C_6$-$C_{14}$)-aryl or Het ring,
  5) —($C_6$-$C_{14}$)-aryl,
  6) Het ring,
  7) —C(O)—O—R10 in which R10 is as defined above,
  8) —C(S)—O—R10 in which R10 is as defined above,
  9) —C(O)—NH—R11 in which R11 is as defined above,
  10) —C(S)—NH—R11 in which R11 is as defined above,
  11) —O—R12 in which R12 is as defined above,
  12) —O—C(O)—R10 in which R10 is as defined above,
  13) —C(O)—R10 in which R10 is as defined above,
  14) —S(O)$_w$—R12 in which R12 is as defined above, and w is the integers zero, 1 or 2,
  15) —N(R15)-R12 in which R15 is as defined above, or
  16) —$SO_2$—N(R12)-R16 in which R12 is as defined above, and R16 is
    a) hydrogen atom,
    b) —($C_1$-$C_6$)-alkyl in which alkyl is unsubstituted or substituted once or twice by —($C_3$-$C_6$)-cycloalkyl, —($C_2$-$C_6$)-alkynyl, —($C_6$-$C_{14}$)-aryl or Het ring,
    c) —C(O)—O—R8 in which R8 is as defined below,
    d) —O—R8 in which R8 is as defined below, or
    e) —($C_3$-$C_6$)-cycloalkyl, or
Y1 and Y2 together form
  a) =O,
  b) =S,
  c) =N—R17 in which R17 is
    c)1) —($C_1$-$C_6$)-alkyl in which alkyl is unsubstituted or substituted once or twice by —($C_3$-$C_6$)-cycloalkyl, —($C_2$-$C_6$)-alkynyl, —($C_6$-$C_{14}$)-aryl or Het ring, or
    c)2) —($C_6$-$C_{14}$)-aryl,
    c)3) hydrogen atom or
    c)4) Het ring, or
  d) =N—O—R17 where R17 is as defined above, or
Y1 and Y2 form together with the carbon atom to which they are each bonded a —($C_3$-$C_7$)-cycloalkyl in which cycloalkyl is unsubstituted or substituted once or twice by —($C_1$-$C_6$)-alkyl, —($C_2$-$C_6$)-alkynyl, —($C_3$-$C_6$)-cycloalkyl, —($C_6$-$C_{14}$)-aryl, or halogen, or
Y1 and Y2 form together with the carbon atom to which they are each bonded a partial structure of the compound of the formula I

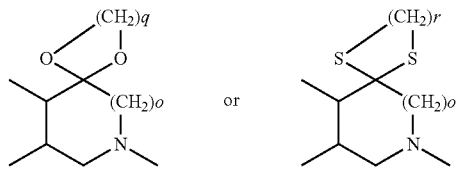

in which
q and r are independently of one another the integer 2, 3 or 4, and the radicals —$(CH_2)_q$— or —$(CH_2)_r$— are unsubstituted or substituted once or twice by —($C_1$-$C_6$)-alkyl, —($C_2$-$C_6$)-alkynyl, —($C_3$-$C_6$)-cycloalkyl, —($C_6$-$C_{14}$)-aryl or halogen,
R2 is hydrogen atom, methyl or ethyl,
R3 and R4 are identical or different and are independently of one another
  1) hydrogen atom,
  2) —($C_1$-$C_6$)-alkyl in which alkyl is unsubstituted or substituted once or twice by —($C_3$-$C_6$)-cycloalkyl, —($C_2$-$C_6$)-alkynyl, —($C_6$-$C_{14}$)-aryl or Het ring,
  3) —C(O)—O—R8 in which R8 is
    a) hydrogen atom,
    b) —($C_1$-$C_6$)-alkyl in which alkyl is unsubstituted or substituted once or twice by —($C_3$-$C_6$)-cycloalkyl, —($C_2$-$C_6$)-alkynyl, —($C_6$-$C_{14}$)-aryl, or Het ring or once to five times by fluorine,
    c) —($C_6$-$C_{14}$)-aryl or
    d) Het ring,
  4) —O—R8 in which R8 has the abovementioned meaning,
  5) —($C_3$-$C_6$)-cycloalkyl,
  6) -halogen,
  7) —$NO_2$,
  8) —CN, or
  9) R3 and R4 form together with the carbon atoms to which they are bonded a —($C_6$-$C_{14}$)-aryl ring in which the ring is unsubstituted or substituted once or twice by G,
  10) R3 and R4 form together with the carbon atoms to which they are bonded a —($C_5$-$C_7$)-cycloalkyl ring, or
  11) R3 and R4 form together with the carbon atoms to which they are bonded a 5-, 6- or 7-membered Het ring, where the ring is unsubstituted or substituted once by G.
The invention further relates to the compound of the formula I, where
A is —($C_0$-$C_4$)-alkylene,
B, D and E are identical or different and are independently of one another —($C_0$-$C_4$)-alkylene or the radical

-B1-B2-B3- in which
B1 is —$(CH_2)_v$— in which v is the integer zero, 1 or 2,
B3 is —$(CH_2)_w$— in which w is the integer zero, 1 or 2, with the proviso that the total of v and w amounts to zero, 1 or 2, and B2 is
1) —C(O)—
2) —($C_2$-$C_4$)-alkenylene,
3) —S(O)$_x$— where x is the integer zero, 1 or 2,
4) —N(R6)- in which R6 is hydrogen atom, methyl or ethyl,
5) —N(R6)-C(Y)— in which Y is oxygen atom or sulfur atom, and R6 is as defined above,
6) —C(Y)—N(R6)- in which Y is oxygen atom or sulfur atom, and R6 is as defined above,
7) —N(R6)-SO$_2$— in which R6 is as defined above,
8) —SO$_2$—N(R6)- in which R6 is as defined above,
9) —N(R6)-SO$_2$—N(R6)- in which R6 is as defined above,
10) —N(R6)-C(Y)—N(R6)- in which Y is oxygen atom or sulfur atom, and R6 is as defined above,
11) —O—C(O)—N(R6)-,
12) —NH—C(O)—O—,
13) —O—,
14) —C(O)—O—,
15) —O—C(O)—,
16) —O—C(O)—O—,
17) —O—CH$_2$—C(O)—,
18) —O—CH$_2$—C(O)—O—,
19) —O—CH$_2$—C(O)—N(R6)- in which R6 is as defined above,
20) —C(O)—CH$_2$—O—,
21) —O—C(O)—CH$_2$—O—,
22) —N(R6)-C(O)—CH$_2$—O— in which R6 is as defined above,
23) —O—(CH$_2$)$_s$—O— in which s is the integer 2 or 3, or
24) —O—(CH$_2$)$_t$—N(R6)- in which t is the integer 2 or 3, and R6 is as defined above,
25) —N(R6)-(CH$_2$)$_u$—O— in which u is the integer 2 or 3, and R6 is as defined above,
26) —N(R6)-N(R6)- in which R6 is as defined above,
27) —N=N—,
28) —N(R6)-CH=N— in which R6 is as defined above,
29) —N=CH—N(R6)- in which R6 is as defined above,
30) —N(R6)-C(R7)=N— in which R6 is as defined above, and R7 is —NH—R6,
31) —N=C(R7)-N(R6)- in which R6 is as defined above, and R7 is —NH—R6 or
32) —($C_2$-$C_6$)-alkynylene, ring1, ring2 or ring3 are identical or different and is independently of one another
1) covalent bond,
2) —($C_6$-$C_{14}$)-aryl in which aryl is a radical from the series phenyl, naphthyl, 1-naphthyl, 2-naphthyl, anthryl or fluorenyl, and are unsubstituted or substituted independently of one another once, twice or three times by G, or
3) 4- to 15-membered Het ring in which the Het ring is a radical from the series acridinyl, azepinyl, azetidinyl, aziridinyl, benzimidazalinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, deca-hydroquinolinyl, dibenzofuranyl, dibenzothiophenyl, dihydrofuran[2,3-b]-tetrahydrofuranyl, dihydrofuranyl, dioxolyl, dioxanyl, 2H,6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, phenanthridinyl, phenanthrolinyl, phenazinyl, phenothiazinyl, phenoxathiinyl, phenoxazinyl, phthalazinyl, piperazinyl, piperidinyl, piperidyl, pteridinyl, purynyl, pyranyl, pyrazinyl, pyroazolidinyl, pyrazolinyl, pyrazolyl, pyridazinyl, pryidooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiomorpholinyl, thiophenyl, triazinyl, 1,2,3-triazolyl, 1,2,4-triazolyl, 1,2,5-triazolyl, 1,3,4-triazolyl and xanthenyl, and these radicals are unsubstituted or substituted independently of one another once, twice or three times by G, with the proviso that at least one of the radicals ring 1, ring2 or ring3 is —($C_6$-$C_{14}$)-aryl or Het ring, where aryl and Het ring are as defined above, ring4 is
1) —($C_6$-$C_{14}$)-aryl in which aryl is a radical from the series phenyl, naphthyl, 1-naphthyl, 2-naphthyl, anthryl or fluorenyl, and is unsubstituted or substituted independently of one another once, twice or three times by G,
2) 4- to 15-membered Het ring in which the Het ring is a radical from the series acridinyl, azepinyl, azetidinyl, aziridinyl, benzimidazalinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, deca-hydroquinolinyl, dibenzofuranyl, dibenzothiophenyl, dihydrofuran[2,3-b]-tetrahydrofuranyl, dihydrofuranyl, dioxolyl, dioxanyl, 2H,6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pryidooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiomorpholinyl, thiophenyl, triazinyl, 1,2,3-triazolyl, 1,2,4-triazolyl, 1,2,5-triazolyl, 1,3,4-triazolyl and xanthenyl, and these radicals are unsubstituted or substituted independently of one another once, twice or three times by G, or
3) is one of the following radicals

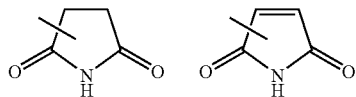

and these radicals are unsubstituted or substituted once by G,

G is
1) hydrogen atom,
2) halogen,
3) =O,
4) —($C_1$-$C_6$)-alkyl in which alkyl is unsubstituted or substituted once, twice or three times by halogen, —($C_3$-$C_6$)-cycloalkyl, —($C_2$-$C_6$)-alkynyl, —($C_6$-$C_{14}$)-aryl or Het ring, where aryl and Het ring are as defined above,
5) —($C_6$-$C_{14}$)-aryl, where aryl is as defined above,
6) Het ring, where Het ring is as defined above,
7) —C(O)—O—R10 in which R10 is
  a) —($C_1$-$C_6$)-alkyl in which alkyl is unsubstituted or substituted once or twice by —($C_3$-$C_6$)-cycloalkyl, —($C_2$-$C_6$)-alkynyl, —($C_6$-$C_{14}$)-aryl, or Het ring where aryl and Het ring are as defined above, or
  b) —($C_6$-$C_{14}$)-aryl or Het ring, where aryl and Het ring are as defined above,
8) —C(S)—O—R10 in which R10 is as defined above,
9) —C(O)—NH—R11 in which R11 is
  a) —($C_1$-$C_6$)-alkyl in which alkyl is unsubstituted or substituted once or twice by —($C_3$-$C_6$)-cycloalkyl, —($C_2$-$C_6$)-alkynyl, —($C_6$-$C_{14}$)-aryl or Het ring, where aryl and Het ring are as defined above, or
  b) —($C_6$-$C_{14}$)-aryl, where aryl is as defined above, or
  c) Het ring, where Het ring is as defined above,
10) is —C(S)—NH—R11 in which R11 is as defined above,
11) —O—R12 in which R12 is
  a) hydrogen atom,
  b) —($C_1$-$C_6$)-alkyl in which alkyl is unsubstituted or substituted once, twice or three times by halogen, —($C_3$-$C_6$)-cycloalkyl, —($C_2$-$C_6$)-alkynyl, —($C_6$-$C_{14}$)-aryl or Het ring, where aryl and Het ring are as defined above,
  c) —($C_6$-$C_{14}$)-aryl, where aryl is as defined above,
  d) Het ring, where Het ring is as defined above,
  e) —C(O)—O—R13 in which R13 is
    e)1) —($C_1$-$C_6$)-alkyl in which alkyl is unsubstituted or substituted once or twice by —($C_3$-$C_6$)-cycloalkyl, —($C_2$-$C_6$)-alkynyl, —($C_6$-$C_{14}$)-aryl, or Het ring, where aryl and Het ring are as defined above, or
    e)2) —($C_6$-$C_{14}$)-aryl or Het ring, where aryl and Het ring are as defined above,
  f) —C(S)—O—R13 in which R13 is as defined above,
  g) —C(O)—NH—R14 in which R14 is
    g)1) —($C_1$-$C_6$)-alkyl in which alkyl is unsubstituted or substituted once or twice by —($C_3$-$C_6$)-cycloalkyl, —($C_2$-$C_6$)-alkynyl, —($C_6$-$C_{14}$)-aryl or Het ring, where aryl and Het ring are as defined above, or
    g)2) —($C_6$-$C_{14}$)-aryl or Het ring, where aryl and Het ring are as defined above, or
  h) —C(S)—NH—R14 in which R14 is as defined above,
12) —C(O)—R10 in which R10 is as defined above,
13) —S(O)$_p$—R12 in which R12 is as defined above, and p is the integers zero, 1 or 2,
14) —$NO_2$,
15) —CN,
16) —N(R15)-R12 in which R12 is as defined above, and R15 is
  a) hydrogen atom,
  b) —($C_1$-$C_6$)-alkyl or
  c) —$SO_2$—($C_1$-$C_6$)-alkyl in which alkyl is unsubstituted or substituted once or twice by —($C_3$-$C_6$)-cycloalkyl, —($C_2$-$C_6$)-alkynyl, —($C_6$-$C_{14}$)-aryl or Het ring, where aryl and Het ring are as defined above, or
17) —$SO_2$—N(R12)-R16 in which R12 is as defined above, and R16 is as defined below, X is —OH or —NH—OH,
m is the integer zero, 1 or 2,
n is the integer zero, 1 or 2, and with the proviso that the total of m and n amounts to 2,
o is the integer 1 or 2,
the partial structure of the compound of the formula I

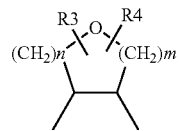

is a radical from the series

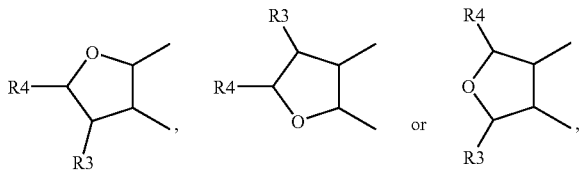

where
R2 is hydrogen atom, methyl or ethyl,
R3 and R4 are identical or different and are independently of one another
1) hydrogen atom,
2) —($C_1$-$C_6$)-alkyl in which alkyl is unsubstituted or substituted once or twice by —($C_3$-$C_6$)-cycloalkyl, —($C_2$-$C_6$)-alkynyl, —($C_6$-$C_{14}$)-aryl or Het ring, where aryl and Het ring are as defined above,
3) —C(O)—O—R8 in which R8 is
  a) hydrogen atom,
  b) —($C_1$-$C_6$)-alkyl in which alkyl is unsubstituted or substituted once or twice by —($C_3$-$C_6$)-cycloalkyl, —($C_2$-$C_6$)-alkynyl, —($C_6$-$C_{14}$)-aryl, or Het ring, where aryl and Het ring are as defined above, or once to five times by fluorine,
  c) —($C_6$-$C_{14}$)-aryl, where aryl is as defined above, or
  d) Het ring, where Het ring is as defined above,
4) —O—R8 in which R8 has the abovementioned meaning,
5) —($C_3$-$C_6$)-cycloalkyl,
6) -halogen,
7) —$NO_2$,
8) —CN, or
9) R3 and R4 form together with the carbon atoms to which they are bonded a ring from the series phenyl, naphthyl, 1-naphthyl, 2-naphthyl, anthryl or fluorenyl, in which the ring is unsubstituted or substituted once or twice by G, or 10) R3 and R4 form together with the carbon atoms to which they are bonded a cyclopentane, cyclohexyl or cycloheptyl ring, or 11) R3 and R4 form together with the carbon atoms to which they are bonded a 5-membered Het ring from the series thiophene, furan, thiazole or oxazole, where the ring is unsubstituted or substituted once by G, Y1 and Y2 are identical or different and are independently of one another
1) hydrogen atom,
2) halogen,
3) —CN,
4) —($C_1$-$C_6$)-alkyl in which alkyl is unsubstituted or substituted once, twice or three times by halogen, —($C_3$-$C_6$)-cycloalkyl, —($C_2$-$C_6$)-alkynyl, —($C_6$-$C_{14}$)-aryl or Het ring, where aryl and Het ring are as defined above,
5) —($C_6$-$C_{14}$)-aryl, where aryl is as defined above,
6) Het ring, where Het ring is as defined above,
7) —C(O)—O—R10 in which R10 is as defined above,
8) —C(S)—O—R10 in which R10 is as defined above,
9) —C(O)—NH—R11 in which R11 is as defined above,
10) —C(S)—NH—R11 in which R11 is as defined above,
11) —O—R12 in which R12 is as defined above,
12) —O—(CO)—R10 in which R10 is as defined above,
13) —C(O)—R10 in which R10 is as defined above,
14) —S(O)$_w$—R12 in which R12 is as defined above, and w is the integers zero, 1 or 2,
15) —N(R15)-R12 in which R15 is as defined above, or
16) —$SO_2$—N(R12)-R16 in which R12 is as defined above, and
R16 is
  a) hydrogen atom,
  b) —($C_1$-$C_6$)-alkyl in which alkyl is unsubstituted or substituted once or twice by —($C_3$-$C_6$)-cycloalkyl, —($C_2$-$C_6$)-alkynyl, —($C_6$-$C_{14}$)-aryl or Het ring, where aryl and Het ring are as defined above,
  c) —C(O)—O—R8 in which R8 is as defined above,
  d) —O—R8 in which R8 is as defined above, or
  e) —($C_3$-$C_6$)-cycloalkyl, or Y1 and Y2 together form
  a) =O,
  b) =S,
  c) =N—R17 in which R17 is
    c)1) —($C_1$-$C_6$)-alkyl in which alkyl is unsubstituted or substituted once or twice by —($C_3$-$C_6$)-cycloalkyl, —($C_2$-$C_6$)-alkynyl, —($C_6$-$C_{14}$)-aryl or Het ring, where aryl and Het ring are as defined above,
    c)2) —($C_6$-$C_{14}$)-aryl, where aryl is as defined above,
    c)3) hydrogen atom or
    c)4) Het ring, where Het ring is as defined above, or
  d) =N—O—R17, where R17 is as defined above, or Y1 and Y2 form together with the carbon atom to which they are each bonded a —($C_3$-$C_7$)-cycloalkyl in which cycloalkyl is unsubstituted or substituted once or twice by —($C_1$-$C_6$)-alkyl, —($C_2$-$C_6$)-alkynyl, —($C_3$-$C_6$)-cycloalkyl, —($C_6$-$C_{14}$)-aryl, where aryl is as defined above, or halogen, or Y1 and Y2 form together with the carbon atom to which they are each bonded a partial structure of the compound of the formula I

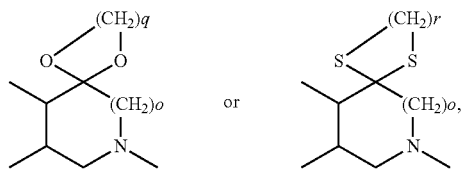

in which q and r are independently of one another the integer 2, 3 or 4, and the radicals —($CH_2$)$_q$— or —($CH_2$)$_r$— are unsubstituted or substituted once or twice by —($C_1$-$C_6$)-alkyl, —($C_2$-$C_6$)-alkynyl, —($C_3$-$C_6$)-cycloalkyl, —($C_6$-$C_{14}$)-aryl, where aryl is as defined above, or halogen.

The invention further relates to the compound of the formula I, where
A is —($C_0$-$C_4$)-alkylene,
B, D and E are identical or different and are independently of one another —($C_0$-$C_2$)-alkylene or the radical

-B1-B2-B3- in which
B1 is —($CH_2$)$_v$— in which v is the integer zero, 1 or 2,
B3 is —($CH_2$)$_w$— in which w is the integer zero, 1 or 2,
with the proviso that the total of v and w amounts to zero, 1 or 2, and
B2 is
1) ethenylene,
2) ethynylene,
3) —C(O)—
4) —N(R6)-C(O)— in which R6 is hydrogen atom, methyl or ethyl,
5) —C(O)—N(R6)- in which R6 is as defined above,
6) —O— or
7) —S—, ring 1, ring2 or ring3 are identical or different and are independently of one another
1) covalent bond,
2) is phenyl or naphthyl and are unsubstituted or substituted independently of one another once or twice by G, or
3) Het ring in which the Het ring is a radical from the series dihydrofuranyl, furanyl, pyridyl, pyrimidinyl, pyrrolyl, thiadiazolyl, thiazolyl or thiophenyl, and are unsubstituted or substituted independently of one another once or twice by G,
with the proviso that at least one of the radicals ring 1, ring2 or ring3 is phenyl, naphthyl or Het ring, ring4 is
1) phenyl or naphthyl and is unsubstituted or substituted independently of one another once or twice by G,
2) Het ring in which the Het ring is a radical from the series benzofuranyl, dihydrofuranyl, dibenzofuranyl, dibenzothiophenyl, furanyl, morpholinyl, piperazinyl, piperidyl, pyridyl, pyrimidinyl, pyridothiophenyl, pyrrolyl, pyrrolidinyl, thiazolyl or thiophenyl, and is unsubstituted or substituted independently of one another once or twice by G, or
3) the following radical

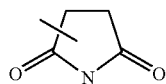

and this radical is unsubstituted or substituted once by G,
G is
1) hydrogen atom,
2) Br, Cl or F, 3) —($C_1$-$C_4$)-alkyl in which alkyl is unsubstituted or substituted once or twice by Br, Cl, F, phenyl, cyclopropyl or Het ring, where Het ring is as defined above for ring4,
4) phenyl,
5) Het ring, where Het ring is as defined above for ring4,
6) —C(O)—O—R10 in which R10 is
  a) —($C_1$-$C_6$)-alkyl in which alkyl is unsubstituted or substituted once or twice by cyclopropyl, phenyl or Het ring, where Het ring is as defined above for ring4,
  b) phenyl, or
  c) Het ring, where Het ring is as defined above for ring4,
7) —C(O)—NH—R11 in which R11 is
  a) —($C_1$-$C_6$)-alkyl in which alkyl is unsubstituted or substituted once or twice by cyclopropyl, phenyl or Het ring, where Het ring is as defined above for ring4,
  b) phenyl, or
  c) Het ring, where Het ring is as defined above for ring4,
8) —O—R12 in which R12 is
  a) hydrogen atom,
  b) —($C_1$-$C_6$)-alkyl in which alkyl is unsubstituted or substituted once, twice or three times by halogen, cyclopropyl, phenyl or Het ring, where Het ring is as defined above for ring4,
  c) phenyl,
  d) Het ring, where Het ring is as defined above for ring4,
  e) —C(O)—O—R13 in which R13 is
    e)1) —($C_1$-$C_6$)-alkyl in which alkyl is unsubstituted or substituted once or twice by cyclopropyl, phenyl or Het ring, where Het ring is as defined above for ring4, or
    e)2) phenyl or Het ring, where Het ring is as defined above for ring4,
  f) —C(S)—O—R13 in which R13 is as defined above, or
  g) —C(O)—NH—R14 in which R14 is
    g)1) —($C_1$-$C_6$)-alkyl in which alkyl is unsubstituted or substituted once or twice by phenyl or Het ring, where Het ring is as defined above for ring4, or
    g)2) phenyl or Het ring, where Het ring is as defined above for ring4,
9) —C(O)—R10 in which R10 is as defined above,
10) —S(O)$_p$—R12 in which R12 is as defined above, and p is the integers 1 or 2,
11) —$NO_2$,
12) —CN or
13) —N(R15)-R12 in which R15 is
  a) hydrogen atom or
  b) —($C_1$-$C_6$)-alkyl, and R12 is as defined above,
X is —OH or —NH—OH,
o is the integer 1 or 2,
R2 is hydrogen atom or methyl,
the partial structure of the compound of the formula I

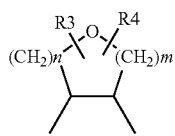

is a radical from the series

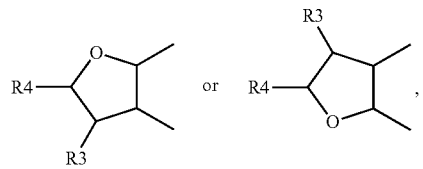

where
R3 and R4 are identical or different and are independently of one another hydrogen atom or methyl,
Y1 and Y2 are identical and are hydrogen atom, or
Y1 and Y2 together form =O or —O—$CH_2$—$CH_2$—O—.
The invention further relates to the compound of the formula I, where
A is a covalent bond or —$CH_2$—$CH_2$—,
B, D and E are identical or different and are independently of one another —($C_0$-$C_2$)-alkylene or the radical

-B1-B2-B3- in which
B1 is —($CH_2$)$_v$— in which v is the integer zero, 1 or 2,
B3 is —($CH_2$)$_w$— in which w is the integer zero, 1 or 2, with the proviso that the total of v and w amounts to zero, 1 or 2, and
B2 is
  1) —C(O)—
  2) ethynylene,
  3) —S—,
  4) —N(R6)-C(O)— in which R6 is hydrogen atom,
  5) —C(O)—N(R6)- in which R6 is hydrogen atom, or
  6) —O—,
ring1, ring2 or ring3 are identical or different and are independently of one another
  1) covalent bond,
  2) is phenyl and are unsubstituted or substituted independently of one another once or twice by G, or
  3) Het ring in which the Het ring is a radical from the series furanyl, pyridyl, pyrimidinyl or thiophenyl, and are unsubstituted or substituted independently of one another once or twice by G,
with the proviso that at least one of the radicals ring 1, ring2 or ring3 is phenyl or Het ring,
ring4 is
  1) phenyl and is unsubstituted or substituted independently of one another once or twice by G,
  2) Het ring in which the Het ring is a radical from the series benzofuranyl, dibenzofuranyl, furanyl, morpholinyl, piperazinyl, piperidinyl, pyridyl, pyrimidinyl, pyridothiophenyl, pyrrolyl, pyrrolidinyl, thiazolyl or thiophenyl and is unsubstituted or substituted independently of one another once or twice by G, or
  3) the following radical

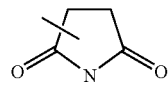

and this radical is unsubstituted or substituted once by G,
G is
  1) hydrogen atom,
  2) Br, Cl or F, 3) —($C_1$-$C_4$)-alkyl in which alkyl is unsubstituted or substituted once, twice or three times by Br, Cl, F, phenyl, cyclopropyl or Het ring, where Het ring is as defined above for ring4,
4) phenyl,
5) Het ring, where Het ring is as defined above for ring4,
6) —C(O)—O—R10 in which R10 is
   a) —($C_1$-$C_6$)-alkyl in which alkyl is unsubstituted or substituted once or twice by cyclopropyl, phenyl or Het ring, where Het ring is as defined above for ring4,
   b) phenyl, or
   c) Het ring, where Het ring is as defined above for ring4,
7) —C(O)—NH—R11 in which R11 is
   a) —($C_1$-$C_6$)-alkyl in which alkyl is unsubstituted or substituted once or twice by cyclopropyl, phenyl or Het ring, where Het ring is as defined above for ring4,
   b) phenyl, or
   c) Het ring, where Het ring is as defined above for ring4,
8) —O—R12 in which R12 is
   a) hydrogen atom,
   b) —($C_1$-$C_6$)-alkyl in which alkyl is unsubstituted or substituted once, twice or three times by halogen, cyclopropyl, phenyl or Het ring, where Het ring is as defined above for ring4,
   c) phenyl,
   d) Het ring, where Het ring is as defined above for ring4,
   e) —C(O)—O—R13 in which R13 is
      e)1) —($C_1$-$C_6$)-alkyl in which alkyl is unsubstituted or substituted once or twice by cyclopropyl, phenyl or Het ring, where Het ring is as defined above for ring4, or
      e)2) phenyl or Het ring, where Het ring is as defined above for ring4,
   f) —C(S)—O—R13 in which R13 is as defined above, or
   g) —C(O)—NH—R14 in which R14 is
      g)1) —($C_1$-$C_6$)-alkyl in which alkyl is unsubstituted or substituted once or twice by phenyl or Het ring, where Het ring is as defined above for ring4, or
      g)2) phenyl or Het ring, where Het ring is as defined above for ring4,
9) —C(O)—R10 in which R10 is as defined above,
10) —S(O)$_p$—R12 in which R12 is as defined above, and p is the integers zero, 1 or 2,
11) —$NO_2$,
12) —CN or
13) —N(R15)-R12 in which R15 is
   a) hydrogen atom or
   b) —($C_1$-$C_6$)-alkyl, and R12 is as defined above,
X is —OH or —NH—OH,
R2 is hydrogen atom,
o is the integer 1 or 2, and the partial structure of the compound of the formula I

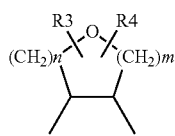

is the radical

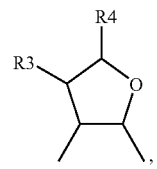

where
R3 and R4 are identical and are hydrogen atom, and
Y1 and Y2 are identical and are hydrogen atom.
The invention further relates to the compound of the formula II, where

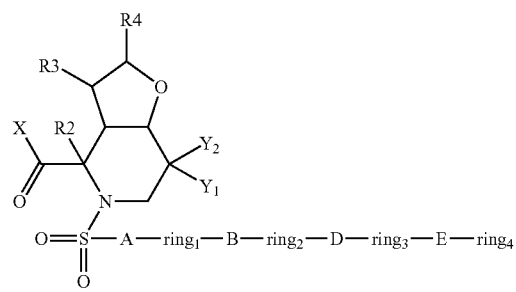

(II)

A is a covalent bond,
B, D and E are identical or different and are independently of one another a covalent bond or the radical —O—,
ring 1, ring2 or ring3 are identical or different and are independently of one another
   1) covalent bond, or
   2) is phenyl and are unsubstituted or substituted independently of one another once or twice by G,
   with the proviso that at least one of the radicals ring 1, ring2 or ring3 is phenyl,
ring4 is phenyl and is unsubstituted or substituted independently of one another once or twice by G,
G is
   1) hydrogen atom,
   2) Br, Cl or F,
   3) —($C_1$-$C_4$)-alkyl in which alkyl is unsubstituted or substituted once, twice or three times by Br, Cl or F,
   4) —$SO_2$-methyl,
   5) —O—($C_1$-$C_4$)-alkyl in which alkyl is unsubstituted or substituted once, twice or three times by Br, Cl or F, or
   6) —CN,
X is —OH or —NH—OH, and
R2, R3, R4, Y1 and Y2 are identical and are hydrogen atom.
The invention further relates to the compound of the formula I from the series
5-(4'-chlorobiphenyl-4-sulfonyl)octahydrofuro[3,2-c]pyridine-4-carboxylic acid,
5-(4'-chlorobiphenyl-4-sulfonyl)octahydrofuro[3,2-c]pyridine-4-(N-hydroxy)-carboxamide,
5-[4-(4-fluorophenoxy)benzenesulfonyl]octahydrofuro[3,2-c]pyridine-4-carboxylic acid,
5-[4-(4-fluorophenoxy)benzenesulfonyl]octahydrofuro[3,2-c]pyridine-4-(N-hydroxy)-carboxamide,
5-[4-(4-cyanophenoxy)benzenesulfonyl]octahydrofuro[3,2-c]pyridine-4-carboxylic acid, 5-[4-(4-methanesulfonylphenoxy)benzenesulfonyl]octahydrofuro[3,2-c]pyridine-4-carboxylic acid,
5-(4'-fluorobiphenyl-4-sulfonyl)octahydrofuro[3,2-c]pyridine-4-(N-hydroxy)-carboxamide,
5-(4'-trifluoromethylbiphenyl-4-sulfonyl)octahydrofuro[3,2-c]pyridine-4-(N-hydroxy)-carboxamide,
5-[4-(4-chlorophenoxy)benzenesulfonyl]octahydrofuro[3,2-c]pyridine-4-(N-hydroxy)-carboxamide,
5-[4-(4-cyanophenoxy)benzenesulfonyl]octahydrofuro[3,2-c]pyridine-4-(N-hydroxy)-carboxamide
or 5-[4-(4-methanesulfonylphenoxy)benzenesulfonyl]octahydrofuro[3,2-c]pyridine-4-(N-hydroxy)carboxamide.

The term "$(C_1-C_6)$-alkyl" means hydrocarbon radicals whose carbon chain is straight-chain or branched and comprises 1 to 6 carbon atoms, for example methyl, ethyl, propyl, isopropyl, butyl, isobutyl, tertiary butyl, pentyl, isopentyl, neopentyl, hexyl, 2,3-dimethylbutane or neohexyl.

The term "—$(C_0-C_4)$-alkylene" means hydrocarbon radicals whose carbon chain is straight-chain or branched and comprises 1 to 4 carbon atoms, for example methylene, ethylene, propylene, isopropylene, isobutylene, butylene or tertiary butylene. "—$C_0$-alkylene" is a covalent bond.

The term "—$(CH_2)_n$—" in which n is the integer zero, 1 or 2" means a covalent bond for n equal to zero, the methylene radical for n equal to 1 and the ethylene radical for n equal to 2. The terms "—$(CH_2)_m$—", "—$(CH_2)_v$—" or "—$(CH_2)_w$—" mean the analogous radical as for "—$(CH_2)_n$—".

The term "—$(C_2-C_4)$-alkenylene" means hydrocarbon radicals whose carbon chain is straight-chain or branched and comprises 2 to 4 carbon atoms and, depending on the chain length, have 1 or 2 double bonds, for example ethenylene, propenylene, isopropenylene, isobutenylene or butenylene; the substituents on the double bond may, as long as the possibility exists in principle, be disposed in E or Z positions.

The term "—$(C_2-C_6)$-alkynylene" means hydrocarbon radicals whose carbon chain is straight-chain or branched and comprises 2 to 6 carbon atoms and, depending on the chain length, have 1 or 2 triple bonds, for example ethynylene, propenylene, isopropynylene, isobuthylinylene, butynylene, pentynylene or isomers of pentynylene or hexynylene or isomers of hexynylene.

If more than one of the radicals A, B, D, E, ring1, ring2 or ring3 in succession are to be in each case a covalent bond, in all cases only one covalent bond remains, and the other covalent bonds are dispensed with. If, for example, A and ring 1 each represent a covalent bond, then one covalent bond is dispensed with, and only one covalent bond remains. If, for example, B, ring2, D and ring3 each represent a covalent bond, then three covalent bonds are dispensed with, and only one covalent bond remains.

The term "$(C_3-C_6)$-cycloalkyl" means radicals such as compounds derived from 3- to 6-membered monocycles such as cyclopropyl, cyclobutyl, cyclopentyl or cyclohexyl.

The term "$(C_5-C_7)$-cycloalkyl" means radicals such as compounds derived from 5- to 7-membered monocycles such as cyclopentyl, cyclohexyl or cycloheptyl.

The term "—$S(O)_x$—, where x is integer zero, 1 or 2" means "—S—" radical for x equal to zero, the "—S(O)—" radical for x equal to 1, and the "—$S(O)_2$—" radical for x equal to 2.

The terms "—$S(O)_p$—" or "—$S(O)_w$—" mean the analogous radicals as for "—$S(O)_x$—".

The term "—$(C_6-C_{14})$-aryl" means aromatic carbon radicals having 6 to 14 carbon atoms in the ring. Examples of —$(C_6-C_{14})$-aryl radicals are phenyl, naphthyl, for example 1-naphthyl, 2-naphthyl, anthryl or fluorenyl. Naphthyl radicals and especially phenyl radicals are preferred aryl radicals.

The term "4- to 15-membered Het ring" or "Het ring" means ring systems having 4 to 15 carbon atoms which are present in one, two or three ring systems connected together and comprise one, two, three or four identical or different heteroatoms from the series oxygen, nitrogen or sulfur. Examples of these ring systems are the radicals acridinyl, azepinyl, azetidinyl, aziridinyl, benzimidazalinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, deca-hydroquinolinyl, dibenzofuranyl, dibenzothiophenyl, dihydrofuran[2,3-b]-tetrahydrofuranyl, dihydrofuranyl, dioxolyl, dioxanyl, 2H, 6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl(benzimidazolyl), isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxothiolanyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidyl, pteridinyl, purynyl, pyranyl, pyrazinyl, pyroazolidinyl, pyrazolinyl, pyrazolyl, pyridazinyl, pryidooxazolyl, pyridoimidazolyl, pyridothiazolyl, pyridothiophenyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiomorpholinyl, thiophenyl, triazinyl, 1,2,3-triazolyl, 1,2,3-triazolyl, 1,2,4-triazolyl, 1,2,5-triazolyl, 1,3,4-triazolyl and xanthenyl.

Preferred Het rings are the radicals benzofuranyl, benzimidazolyl, benzoxazolyl, benzothiazolyl, benzothiophenyl, 1,3-benzodioxolyl, quinazolinyl, quinolinyl, quinoxalinyl, chromanyl, cinnolinyl, furanyl; such as 2-furanyl and 3-furanyl; imidazolyl, indolyl, indazolyl, isoquinolinyl, isochromanyl, isoindolyl, isothiazolyl, isoxazolyl, oxazolyl, phthalazinyl, pteridinyl, pyrazinyl, pyrazolyl, pyridazinyl, pyridoimidazolyl, pyridopyridinyl, pyridopyrimidinyl, pyridyl; such as 2-pyridyl, 3-pyridyl or 4-pyridyl; pyrimidinyl, pyrrolyl; such as 2-pyrrolyl and 3-pyrrolyl; purinyl, thiazolyl, tetrazolyl or thienyl; such as 2-thienyl and 3-thienyl.

The term "R3 and R4 form together with the carbon atoms to which they are bonded a 5-, 6- or 7-membered Het ring" means ring systems having 5, 6 or 7 carbon atoms which comprise one, two or three identical or different heteroatoms from the series oxygen, nitrogen or sulfur, such as azepane, 1,4-diazepane, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, morpholine, 1,2-oxathiolane, 1,4-oxazepane, 1,2-oxazine, 1,3-oxazine, 1,4-oxazine, oxazole, oxepane, piperazine, piperidine, pyrane, pyrazine, pyrazole, pyrazoline, pyrazolidine, pyrazine, pyrazinone, pyridazine, pyridazone, pyridine, pyridone, pyrimidine, pyrimidone, pyrrole, pyrrolidine, pyrrolidinone, pyrroline, tetrahydrofuran, tetrahydropyran, tetrahydropyridine, thiadiazine, thiadiazole, 1,4-thiazepane, 1,2-thiazine, 1,3-thiazine, 1,4-thiazine, 1,3-thiazole, thiazole, thiazolidine, thiazoline, thiepane, thiomorpholine, thiophene, thiopyran, 1,2,3-triazine, 1,2,4-triazine, 1,3,5-triazine, 1,2,3-triazole or 1,2,4-triazole.

The term "halogen" means fluorine, chlorine, bromine or iodine.

The following structural formulae emerge for the compound of the formula I:

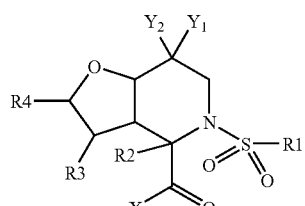

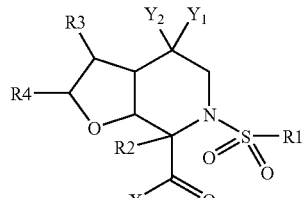

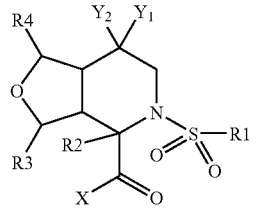

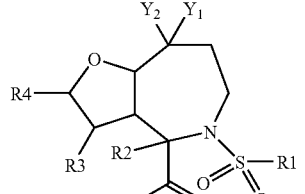

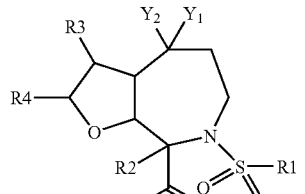

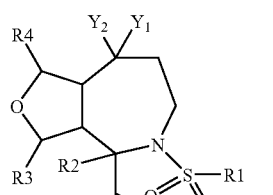

The invention further relates to a method for preparing the compound of the formula I and/or a stereoisomeric form of the compound of the formula I and/or a physiologically tolerated salt of the compound of the formula I, which comprises a) a compound of the formula IV

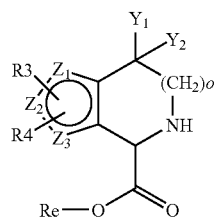

(IV)

in which Re is a hydrogen atom or an ester protective group, the radicals $Y_1$, $Y_2$, $R_3$, $R_4$ and o are as defined in the compound of the formula I, and the partial structure of the compound of the formula I

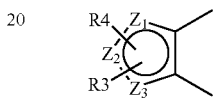

is an unsaturated ring having 5 ring atoms, where one of the ring atoms $Z_1$, $Z_2$ or $Z_3$ is an oxygen atom, and the two other ring atoms are carbon atoms which are substituted independently of one another by $R_3$ or $R_4$, being converted by hydrogenation under suitable conditions into a compound of the formula V

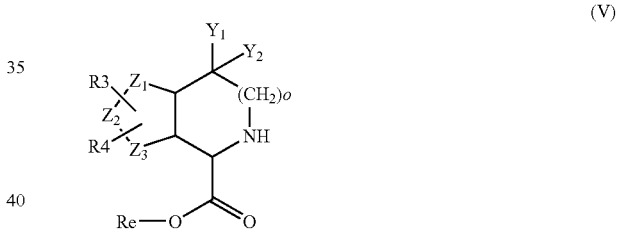

(V)

in which the partial structure of the compound of the formula I

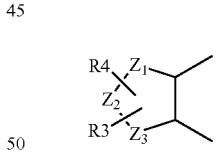

is a saturated ring having 5 ring atoms, where one of the ring atoms $Z_1$, $Z_2$ or $Z_3$ is an oxygen atom, and the two other ring atoms are carbon atoms which are substituted independently of one another by $R_3$ or $R_4$, and the radicals $Y_1$, $Y_2$, $R_3$, $R_4$ and o are as defined in the compound of the formula IV, b) subsequently the compound of the formula V being reacted with a compound of the formula VI (VI)

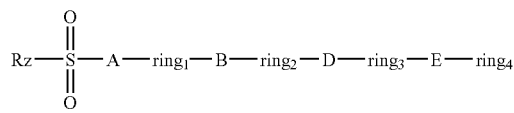

in which A, B, D, E and ring1, ring2, ring3, ring4 are as defined in formula I, and in which Rz is chlorine atom, bromine atom, imidazoyl or OH, in the presence of a base or after silylation with a suitable silylating agent or with a suitable dehydrating agent in the case where Rz=OH to give a compound of the formula VII

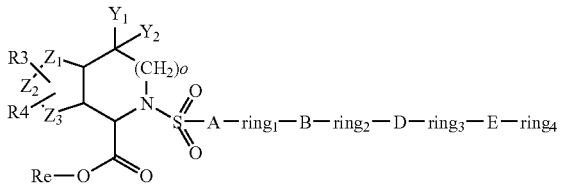

(VII)

in which A, B, D, E, Re and ring1, ring2, ring3 and ring4 are as defined above, and b) in the case where Re=ester, a compound of the formula VII prepared as in a) being reacted with an alkali metal hydroxide solution such as NaOH or LiOH and subsequent acid treatment to give the carboxylic acid of the invention of the formula I in which X is OH, with modifications in one of the side chains of the rings ring1-ring4 having been undertaken where appropriate beforehand; or said ester being converted by treatment with mineral acids such as hydrochloric acid into the free carboxylic acid of the formula VIII

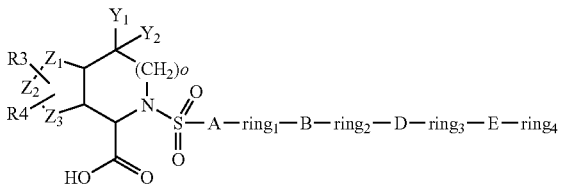

(VIII)

or subsequently the compound of the formula VIII being converted into the hydroxamic acid in which X is NH—OH, of the formula I, c) a compound of the formula I prepared by method a), or a suitable precursor of the formula I which, owing to its chemical structure, occurs in enantiomeric forms, being fractionated into the pure enantiomers by salt formation with enantiopure acids or bases, chromatography on chiral stationary phases or derivatization with chiral enantiopure compounds such as amino acids, separation of the diastereomers obtained in this way, and elimination of the chiral auxiliary groups, or d) the compound of the formula I prepared by methods b) or c) either being isolated in free form or, in the case where acidic or basic groups are present, being converted into physiologically tolerated salts.

Compounds of the type of formulae IV to VIII represent bicyclic compounds which comprise a functionalized ring having six ring atoms or a ring having seven ring atoms. The second ring is an unsaturated furan (formula IV) or a saturated, heterocyclic tetrahydrofuran system, where the oxygen atom may in accordance with formula I be at any of the three possible positions. Both rings may also be substituted in accordance with formula I.

Compounds of the type of formula IV can be prepared by known methods. For example, compounds with o=1 can be prepared by known methods from the corresponding furan derivatives. The preparation of these compounds is known to the skilled worker and can take place by various methods. The synthesis of furans has been described for example in: Science of Synthesis 9, 183-285 (2002). A useful method for preparing bicyclic starting compounds starts for example from 2-aminoethyl- or 3-aminopropyl-(2- or 3-furyl) derivatives. Cyclization takes place in a Pictet-Spengler-type reaction under acidic conditions with glyoxylic acids or esters thereof. This reaction is described for example in J. Med. Chem. 37, 2138-2144 (1994). However, it is also possible to use other methods for constructing the analogous furan system leading to the tetrahydrofurans of the invention. The skilled worker will select the suitable syntheses depending in particular on the substituents or ring size. Synthesis of the furans is followed by conversion into the tetrahydrofurans. This usually takes place by catalytic hydrogenation. A large number of methods are described in the literature. Selection of the suitable conditions depends on the reactivity of the basic structure, any functional groups or substituents present, and the extent to which chiral compounds are also to be generated through the use of chiral auxiliaries and catalysts. Thus, the following catalysts and reagents are frequently described for the hydrogenation, but only one exemplary literature reference is mentioned in each case: H2, Pd/C (e.g. in Arch. Pharm. 336, 381-4 (2003) or Synthesis 2004, pp. 2069-2077); also as transfer hydrogenation with ammonium formate: Heterocycles 35, 737-754 (1993)), Na in liquid ammonia (e.g. J. Heterocycl. Chem. 37, 751-55 (2000)); Raney nickel (Synth. Commun. 25, 2895-2900 (1995)) or Ni on support materials (J. Mol. Catal. 57, 397 (1990); J. Heterocycl. Chem. 3, 101 (1966)); Rh on support materials (J. Org. Chem. 37, 4260 (1972)); PdO (Org. Synth. 1943, II, 566)); LiAlH4 can likewise be employed (J. Chem. Soc. 1957, p. 1788). Methods for enantioselective homogeneous hydrogenation with specific Rh catalysts (Monatsh. Chem. 131, 1335-1343 (2000), or enantiodifferentiating hydrogenation with specifically modified Raney nickel (Chem. Lett. 1999, pp. 1055-56) are also to be found. Furan derivatives still having substituents Y1 and Y2 can also be obtained by other methods. For example, an analogous synthesis of the compound with Y1 and Y2 equal to C=O is to be found in WO2002/100860. Compounds of this type represent important starting materials and can be converted by a large number of methods known to the skilled worker into compounds with other substituents Y1 and Y2. In this case too, the furan is converted into the tetrahydrofuran at a suitable stage to give compounds of the formula I.

Tetrahydrofuran syntheses have been described previously and are known to the skilled worker. It is likewise possible to prepare the compounds of the invention by suitable choice of starting materials and substituents without using furans as intermediates. Novel syntheses are to be found for example in Progress in Heterocyclic Chemistry 14, 139 (2002) or Progress in Heterocyclic Chemistry 7, 130 (1995).

It is possible to employ as ester protective group Re the groups used as protective groups for esters in "Protective Groups in Organic Synthesis", T. H. Greene, P. G. M. Wuts, Wiley-Interscience, 1999. Preferred ester protective groups are for example methyl, ethyl, isopropyl, tertiary butyl or benzyl.

It may be worthwhile under certain conditions to employ compounds of the formula IV in N-protected state. For example, compounds protected in this way can be purified better than the free imino acids, and they can likewise be employed better for preparing the enantiomerically or diastereomerically pure compounds. Protective groups which can be employed for the amino group are the groups described in "Protective Groups in Organic Synthesis", T. H. Greene, P. G. M. Wuts, Wiley-Interscience, 1999. Preferred amino or imino protective groups are for example Z, Boc, Fmoc, Aloc, acetyl, trifluoroacetyl, benzoyl, benzyl and similar protective groups.

The starting materials and reagents employed can either be prepared by known methods or be obtained by purchase.

The reactions take place as described in WO97/18194. The reaction in step a) of the method takes place in the presence of a base such as KOH, NaOH, LiOH, N-methylmorpholine (NMM), N-ethylmorpholine (NEM), triethylamine (TEA), diisopropylethylamine (DIPEA), pyridine, collidine, imidazole or sodium carbonate, in solvents such as tetrahydrofuran (THF), dimethylformamide (DMF), dimethylacetamide, dioxane, acetonitrile, toluene, chloroform or methylene chloride, or else in the presence of water. In the case where the reaction with use of silylating agents, for example N,O-bis(trimethylsilyl)acetamide (BSA) or N,O-bis(trimethylsilyl)trifluoroacetamide (BSTFA) is employed for silylation of the imino acid in order subsequently to carry out the sulfonamide formation as described.

In step c) of the method, the compound of the formula I is, if it occurs as mixture of diastereomers or enantiomers or results as mixtures thereof in the chosen synthesis, separated into the pure stereoisomers, either by chromatography on an optionally chiral support material or, if the racemic compound of the formula I is capable of salt formation, by fractional crystallization of the diastereomeric salts formed with an optically active base or acid as auxiliary. Examples of suitable chiral stationary phases for thin-layer or column chromatographic separation of enantiomers are modified silica gel supports (so-called Pirkle phases) and high molecular weight carbohydrates such as triacetylcellulose. For analytical purposes it is also possible to use, after appropriate derivatization known to the skilled worker, gas chromatographic methods on chiral stationary phases. To separate enantiomers of the racemic carboxylic acids, diastereomeric salts differing in solubility are formed using an optically active, usually commercially available, base such as (−)-nicotine, (+)- and (−)-phenylethylamine, quinine bases, L-lysine or L- and D-arginine, the less soluble component is isolated as solid, the more soluble diastereomer is deposited from the mother liquor, and the pure enantiomers are obtained from the diastereomeric salts obtained in this way. It is possible in the same way in principle to convert the racemic compounds of the formula I containing a basic group such as an amino group with optically active acids such as (+)-camphor-10-sulfonic acid, D- and L-tartaric acid, D- and L-lactic acid and (+) and (−)-mandelic acid into the pure enantiomers. Chiral compounds containing alcohol or amine functions can also be converted with appropriately activated or, where appropriate, N-protected enantiopure amino acids into the corresponding esters or amides, or conversely chiral carboxylic acids can be converted with carboxyl-protected enantiopure amino acids into the amides or with enantiopure hydroxy carboxylic acids such as lactic acid into the corresponding chiral esters. The chirality of the amino acid or alcohol residue introduced in enantiopure form can then be utilized for separating the isomers by carrying out a separation of the diastereomers which are now present by crystallization or chromatography on suitable stationary phases, and then eliminating the included chiral moiety again by suitable methods.

A further possibility with some of the compounds of the invention is to employ diastereomerically or enantiomerically pure starting materials to prepare the structures. It is thus possible where appropriate also to employ other or simplified methods for purifying the final products. These starting materials have previously been prepared enantiomerically or diastereomerically pure by methods known from the literature. For example, in the method for preparing octahydrofuro[3,2-c]pyridine-4-carboxylic acid it is possible to employ either directly the 4,5,6,7-tetrahydrofuro[3,2-c]pyridine-4-carboxylic acid, as detailed and cited above. In this case it is possible through the presence of 3 stereocenters for a maximum of 8 stereoisomers (4 enantiomeric pairs of diastereomers) to be formed. However, certain stereoisomers are greatly preferred owing to the manner of preparation, for example hydrogenation, and the ring strain in the bicyclic system. Thus, it ought to be possible, as described in the literature, to achieve a strong preference for addition of hydrogen at the positions where the rings are connected through suitable choice of the hydrogenation conditions (catalyst, pressure, solvent, temperature) for example. It is thus possible under the indicated conditions to achieve formation of the cis-connected rings. It therefore then remains to determine the position of the carboxylic acid; the number of possible stereoisomers would already be restricted to 4. Owing to the nature of the hydrogenation mechanism, addition of the hydrogens on the same side as that of the bridgehead hydrogens can take place particularly easily, i.e. a further restriction in the possibility of isomer formation is to be expected therewith. It would thus be possible in the most favorable case to expect formation of only one pair of enantiomers. It should then be possible to fractionate this into the enantiomers by the abovementioned methods. However, it must also be assumed in these considerations that complete stereoselection never takes place; on the contrary, greater or lesser proportions of the other isomers are virtually always also produced, or can be detected even in miniscule quantities by suitable methods. In the case where enantiomerically pure tetrahydrofuro[3,2-c]pyridine-4-carboxylic acid derivatives are employed, it would be expected that only preferred stereoisomers will again be formed; in the case mentioned, there should be a strong preference for a single enantiomer because, in the hydrogenation process under analogous conditions leading to cis connection of the rings in the hydrogenation, in this case addition of the H atoms may again take place only from one side, and thus analogous products are formed. The identity of the structures can be established by suitable 2D-NMR experiments, X-ray structural analysis such as, for instance, crystal structure analysis or cocrystallization or others, and comparative analysis or chemical derivatization and suitable analysis or chemical derivatization leading to known and described isomers.

Another possibility for synthesizing enantiomerically or diastereomerically pure compounds is to employ starting materials with suitable chiral substituents in order to achieve through the chiral substituents an induction of chirality at other chirality centers. For example, chiral glyoxylic esters could be employed in Pictet-Spengler cyclizations in order to obtain chiral furan derivatives and then to hydrogenate the latter as already mentioned above.

Acidic or basic products of the compound of the formula I may be in the form of their salts or in free form. Pharmacologically acceptable salts are preferred, for example alkali metal or alkaline earth metal salts or hydrochlorides, hydrobromides, sulfates, hemisulfates, all possible phosphates, and salts of amino acids, natural bases or carboxylic acids.

The preparation of physiologically tolerated salts from the compounds of the formula I which are capable of salt formation, including the stereoisomeric forms thereof, in step d) of the method takes place in a manner known per se. The compounds of the formula I form stable alkali metal, alkaline earth metal or optionally substituted ammonium salts with basic reagents such as hydroxides, carbonates, bicarbonates, alcoholates, and ammonia or organic bases, for example trimethyl- or triethylamine, ethanolamine, diethanolamine or triethanolamine, trometamol or else basic amino acids, for instance lysine, ornithine or arginine. If the compounds of the formula I have basic groups, it is also possible to prepare stable acid addition salts with strong acids. Suitable for this purpose are both inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic, or trifluoroacetic acid.

The invention also relates to medicaments which have an effective content of at least one compound of the formula I and/or of a physiologically tolerated salt of the compound of the formula I and/or an optionally stereoisomeric form of the compound of the formula I, together with a pharmaceutically suitable and physiologically tolerated carrier, additive and/or other active ingredients and excipients.

Because of the pharmacological properties, the compounds of the invention are suitable for the selective prophylaxis and therapy of all disorders in the progression of which an enhanced activity of metalloproteinases are involved. These include degenerative joint disorders such as osteoarthroses, spondyloses, chondrolysis following joint trauma or prolonged joint immobilization after meniscus or patella injuries or ligament tears. They also include connective tissue disorders such as collagenoses, periodontal disorders, wound-healing disturbances and chronic disorders of the locomotor system such as inflammatory, immunologically or metabolically related acute and chronic arthritides, arthropathies, myalgias and disturbances of bone metabolism. The compounds of the formula I are further suitable for the treatment of ulceration, atherosclerosis and stenoses. The compounds of the formula I are further suitable for the treatment of inflammations, cancers, tumor metastasis, cachexia, anorexia, heart failure and septic shock. The compounds are likewise suitable for the prophylaxis of myocardial and cerebral infarctions.

The medicaments of the invention can be administered by oral, inhalational, rectal or transdermal administration or by subcutaneous, intraarticular, intraperitoneal or intravenous injection. Oral administration is preferred.

The invention also relates to a process for producing a medicament which comprises converting at least one compound of the formula I with a pharmaceutically suitable and physiologically tolerated carrier and, where appropriate, further suitable active ingredients, additives or excipients into a suitable dosage form.

Examples of suitable solid or pharmaceutical formulations are granules, powders, coated tablets, tablets, (micro)capsules, suppositories, syrups, oral solutions, suspensions, emulsions, drops or injectable solutions, and products with protracted release of active ingredient, in the production of which conventional excipients such as carriers, disintegrants, binders, coating agents, swelling agents, glidants or lubricants, flavorings, sweeteners and solubilizers are used. Excipients which are frequently used and which may be mentioned are magnesium carbonate, titanium dioxide, lactose, mannitol and other sugars, talc, milk protein, gelatin, starch, cellulose and its derivatives, animal and vegetable oils such as fish liver oil, sunflower, peanut or sesame oil, polyethylene glycol and solvents such as, for example, sterile water and monohydric or polyhydric alcohols such as glycerol.

The pharmaceutical products are preferably produced and administered in dosage units, each unit comprising as active ingredient a particular dose of the compound of the invention of the formula I. In the case of solid dosage units such as tablets, capsules, coated tablets or suppositories, this dose can be up to about 1000 mg, but preferably about 50 to 300 mg, and in the case of solutions for injection in ampoule form up to about 300 mg, but preferably about 10 to 100 mg.

The daily doses indicated for the treatment of an adult patient weighing about 70 kg are from about 2 mg to 1000 mg of active ingredient, preferably about 50 mg to 500 mg, depending on the activity of the compound of the formula I. However, in some circumstances, higher or lower daily doses may also be appropriate. The daily dose may be administered both by administration once a day in the form of a single dosage unit or else a plurality of smaller dosage units, and by administration more than once a day in divided doses at defined intervals.

Final products are usually determined by mass spectroscopic methods (FAB-, ESI-MS) and $^1$H-NMR (500 MHz, in DMSO-D6), indicating in each case the main peak or the two main peaks. Temperatures are stated in degrees Celsius, RT means room temperature (21° C. to 24° C.). Abbreviations used are either explained or comply with usual conventions.

The invention is explained below in more detail by means of examples.

General Method 1: Sulfonamide from Sulfonyl Chloride and Carboxylic Acid

The carboxylic acid (6.45 mmol) was dissolved in 20 ml of dimethylformamide (DMF) and, at 0° C., 3 equivalents of a 3N NaOH solution (6.45 ml) were added. After 10 min, a solution of the arylsulfonyl chloride (1.1 equivalents, 7.1 mmol) in 10 to 15 ml of DMF was slowly added dropwise and, after room temperature (RT) is reached, the mixture is stirred at temperatures between 20° C. and 80° C. for a maximum of 12 hours (h). The exact time depends on the conversion which has taken place and which was established by mass spectroscopy. The solvent was then removed under reduced pressure. This was followed by an aqueous workup (shaking with 1N HCl and saturated NaCl solution, drying of the organic phase such as ethyl acetate, methylene chloride or chloroform with magnesium sulfate or sodium sulfate, and then concentration). The crude product was either immediately reacted further or purified by chromatography.

General Method 2: Sulfonamide from Sulfonyl Chloride and Carboxylic Acid

The carboxylic acid was dissolved in 0.5-2 molar NaOH, possibly with addition of 10-50% tetrahydrofuran (THF) or DMF. Acid chloride (1-1.2 equivalents, preferably 1.1) was dissolved in THF (concentration 0.05 to 1 M) and slowly added dropwise. 2N NaOH was automatically added in an autotitrator at RT to keep the pH constant. Adjusted value of pH: 8 to 12, preferably 9 to 11. After the reaction was complete, identifiable by no further NaOH consumption, the organic cosolvent was removed in a rotary evaporator, and the aqueous solution or suspension was mixed with ethyl acetate and acidified with 1N HCl. After removal of the organic phase and renewed extraction of the aqueous phase with ethyl acetate, the organic phases were combined and dried over sodium sulfate, and then the solvent was removed under reduced pressure. The crude product was either immediately reacted further or purified by chromatography.

General Method 3: Sulfonamide from Sulfonyl Chloride and Carboxylic Acid

This method is particularly suitable for reacting biphenylethylsulfonyl chloride with imino carboxylic acids (see Example 6 and Example 7) or similar sulfonyl chlorides which are relatively labile to hydrolysis.

8 mmol of the imino acid were dissolved or suspended in 30 ml of acetonitrile. At RT and under an inert gas ($N_2$), 2.3 g (9 mmol) of BSTFA (bis(trimethylsilyl)-trifluoroacetamide) were added, and the mixture was heated under reflux for 2 h. 2.84 g (9 mmol) of 4-chlorobiphenylethanesulfonyl chloride, dissolved in 30 ml of acetonitrile, were added to this solution, which was then heated under reflux conditions for 3 h. Cooling of the reaction mixture was followed by addition of aqueous 1 N HCl and stirring for 1 h, and the solvent was removed under reduced pressure in a rotary evaporator and then ethyl acetate or chloroform was added, and the organic phase was separated off, extracted with saturated NaCl solution, dried over sodium sulfate and concentrated under reduced pressure. Depending on the purity of the reaction product, immediate further reaction thereof was possible, or previous chromatography on silica gel was necessary.

General Method 4: Preparation of the Hydroxamic Acid from Carboxylic Acid Via Chloroformate Activation The sulfonated carboxylic acid was dissolved in 10 ml of DMF and. at 0° C., 1.1 equivalents of ethyl chloroformate, 2.2 equivalents of N-ethylmorpholine and—after a preactivation time of 30 min to 1 h—3 equivalents of trimethylsilylhydroxylamine were added. Heating at 80° C. for at least 4 h was followed by removal of the solvent under reduced pressure and purification of the crude product by chromatographic methods.

General Method 5: Preparation of the Hydroxamic Acid by the Corresponding Carbonyl Chloride The sulfonated carboxylic acid was introduced into dry chloroform (ethanol-free) (about 5 ml for 0.5 mmol) and, at RT, 3 equivalents of oxalyl chloride were added. The mixture was then heated at 45° C. for about 30 min. To check chloride formation, a small sample was taken out of the reaction flask and mixed with a little benzylamine in THF. It was possible to identify completion of the reaction from quantitative formation of benzylamide, and the carboxylic acid was no longer detectable (check by HPLC-MS). Heating for a longer time or heating under reflux conditions is necessary where appropriate. The solvent was then removed by distillation under reduced pressure, and the residue was taken up in dry toluene and again concentrated in a rotary evaporator several times. The acid chloride was then again taken up in chloroform (10 ml per 0.5 mmol) and, at RT, 3 equivalents of O-trimethylsilylhydroxylamine were added. After a reaction time of at least 30 min (reaction check by HPLC-MS), the reaction mixture was evaporated under reduced pressure and the residue was immediately purified by chromatography.

Specific Methods

EXAMPLE 1

Octahydrofuro[3,2-c]pyridine-4-carboxylic acid 2.5 g of the appropriate furan derivative 4,5,6,7-tetrahydrofuro[3,2-c]pyridine-4-carboxylic acid (167.16; 14.96 mmol) were dissolved in methanol (MeOH; 45 ml) and hydrogenated with 0.5 g of rhodium on aluminum oxide at 5 bar and RT for 38 h. Following a check of the reaction, the catalyst was then removed by filtration and washed with acetonitrile, and the remaining yellowish solution was, after addition of 15 ml of 1 M HCl, concentrated under reduced pressure. The aqueous residue was frozen and freeze dried.

Yield: 1.51 g (53% of theory)

EXAMPLE 2

N-(4-Chlorobiphenylsulfonyl)-4,5,6,7-tetrahydrofuro [3,2-c]pyridine-4-carboxylic acid The imino acid 4,5,6,7-tetrahydrofuro[3,2-c]pyridine-4-carboxylic acid (250 mg, 1.5 mmol) prepared by the literature method indicated above was dissolved or suspended in acetonitrile (15 ml) and heated together with N,O-bis-(trimethylsilyl)acetamide (671 mg, 0.82 ml, 3.3 mmol) under reflux for 45 min. Then, after cooling, 4-chlorobiphenylsulfonyl chloride (473.8 ml, 1.65 mmol, 1.1 eq.), dissolved in 5 ml of acetonitrile, was added. After a further hour under reflux, the reaction mixture was concentrated under reduced pressure, taken up in ethyl acetate and extracted with dilute hydrochloric acid or saturated sodium chloride solution. The combined organic phases were dried over sodium sulfate. An oily residue remained after removal of the solvent and became solid under oil pump vacuum, and was sufficiently pure for further reactions.

Yield: 455 mg g (73% of theory). Analytical data: see Table 1.

EXAMPLE 3

N-(4-Chlorobiphenylsulfonyl)-4,5,6,7-tetrahydrofuro [3,2-c]pyridine-4-N-hydroxycarboxamide The carboxylic acid from Example 2 (430 mg, 1.03 mmol) was dissolved in 20 ml of chloroform. Then, oxalyl chloride (2.176 g, 17.14 mmol, 1.501 ml) was added dropwise over the course of 10 min, and the resulting reaction mixture was heated at 45° C. for one hour. After this time, to check the reaction by HPLC-MS, a small sample of the reaction mixture (0.1 ml) was removed and mixed with 0.05 ml of benzylamine. The solvent was then distilled out under reduced pressure, and the resulting oily residue was entrained with toluene to remove any oxalyl chloride residues or HCl and was left under reduced pressure for 15 min. It was then again taken up in chloroform (15 ml) and, at RT, O-trimethylsilylhydroxylamine (325.1 mg, 3.09 mmol, 0.378 ml) was added. After 2 hours, the solvent was removed under reduced pressure and the residue was dissolved in a small amount of an acetonitrile-water-0.01% trifluoroacetic acid mixture for direct preparative RP-HPLC. Product fractions were combined, acetonitrile was removed under reduced pressure, and the remaining aqueous phase was freeze dried. Yield: 20 mg (7% of theory, also obtained are 110 mg of an impure fraction analytical data: see Table 1.

The following examples were prepared in analogy to the above-mentioned general or specific methods. Table 1 shows the results.

TABLE 1

| Example | Structure | Molecular weight | ES+ | 1H-NMR |
|---|---|---|---|---|
| 1 | 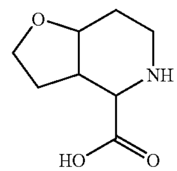 | 171.10 | 172.20 | 1.4-2.05 (3 m, 3 H); 2.6-4.1 (mm, 8 H, the NMR signal of H₂O overlaps with the signal of the substance) |
| 2 | 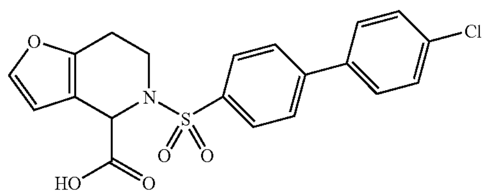 | 417.87 | 418.03 | 2.55; 3.55; 4.10 (3 m, 4 H); 5.39; 6.45 (2 s, 2 H); 7.53; 7.82 (2 m, 9 h); 13.2 (s, 1 H) |
| 3 | 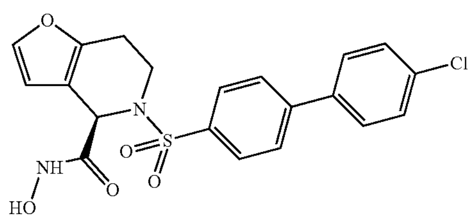 | 432.89 | 433.06 | 2.55; 3.85; 4.10 (3 m, 4 H); 5.20; 6.35 (2 s, 2 H); 7.50; 7.82 (2 m, 9 h); 11.0 (s, 1 H) |
| 4 | 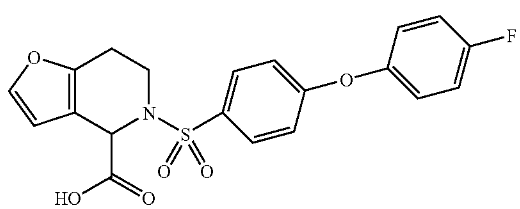 | 417.41 | 418.04 | 2.55; 3.55; 4.10 (3 m, 4 H, the NMR-signal of H₂O overlaps with the signal of the substance); 5.42; 6.45 (2 s, 2 H); 7.0; 7.18 (2 m, 4 H); 7.30 (m, 2 H); 7.51 (s, 1 H); 7.8 (m, 2 H); 13.2 (s, 1 H) |
| 5 | 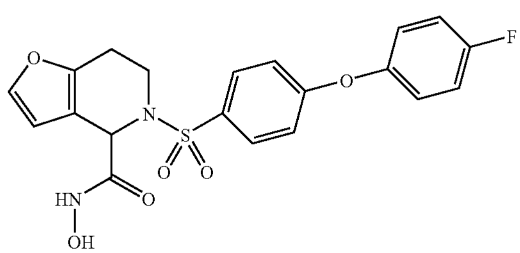 | 432.43 | 433.07 | 2.55; 3.8; 4.0 (3 m, 4 H, the NMR signal of H₂O overlaps with the signal of the substance); 5.12; 6.33 (2 s, 2 H); 7.0; 7.18 (2 m, 4 H); 7.30 (m, 2 H); 7.51 (s, 1 H), 7.74 (m, 2 H); 11.2 (s, 1 H) |
| 6 | 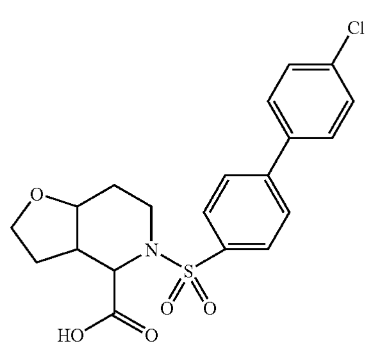 | 421.90 | 422.25 | 1.5-2.15 (4 m, 3-4 H); 2.55 (m, 1 H); 3.25-3.8 (4 m, 4-5 H, the NMR signal of H₂O overlaps with the signal of the substance); 4.33 (d, 1 H); 7.6, 7.8 (dd, 4 H); 7.9 (dd, br, 4 H); 12.9 (s, 1 H) |

TABLE 1-continued

| Example | Structure | Molecular weight | ES+ | 1H-NMR |
|---|---|---|---|---|
| 7 | 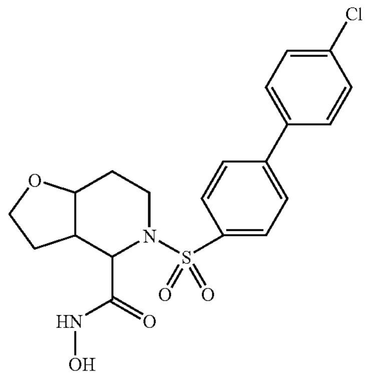 | 436.92 | 437.28 | 1.5-2.0 (3 m, 3-4 H); 2.4 (m, 1 H); 3.2-3.8 (5 m, 4-5 H, the NMR signal of H₂O overlaps with the signal of the substance); 4.2 (d, 1 H); 7.1, 7.8 (dd, 4 H); 7.2, 7.3 (dd, br, 4 H); 10.8 (s, 1 H) |
| 8 | CHIRAL | 438.93 | | from chiral fractionation of Example 7 |
| 9 | CHIRAL | 438.93 | | from chiral fractionation of Example 7 |
| 10 | 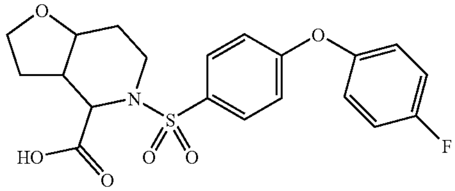 | 421.45 | 422.26 | 1.5-2.1 (4 m, 4 H); 2.55 (m, 1 H); 3.25-3.85 (4 m, 4-5 H, the NMR signal of H₂O overlaps with the signal of the substance); 4.28 (d, 1 H); 7.1 (d, 2 H); 7.2-7.35 (2 m, 4 H); 7.8 (d, br, 2 H); 12.9 (s, 1 H) |
| 11 | 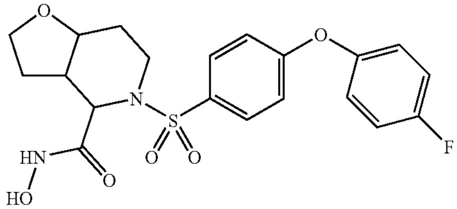 | 436.46 | 437.25 | 1.5-2.0 (3 m, 4 H), 2.4 (m, 1 H); 3.4-3.85 (4 m, 4-5 H, the NMR signal of H₂O overlaps with the signal of the substance); 4.23 (d, 1 H); 7.1 (d, 2 H); 7.6-7.95 (4 "d", 8 H); 10.8 (s, 1 H) |

TABLE 1-continued

| Example | Structure | Molecular weight | ES+ | 1H-NMR |
|---|---|---|---|---|
| 12 | CHIRAL | 438.48 | | from chiral fractionation of Example 11 |
| 13 | CHIRAL | 438.48 | | from chiral fractionation of Example 11 |
| 14 | 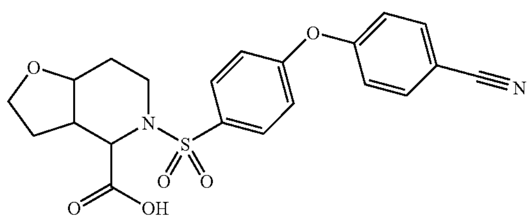 | 428.47 | 428.10 | 1.5-2.15 (4 m, 4 H); 2.5 (m, 1 H); 3.25-3.80 (4 m, 4-5 H, the NMR signal of $H_2O$ overlaps with the signal of the substance); 4.05 (m, 1 H); 4.3 (d, 1 H); 7.0-7.5 (4 m, 4 H); 7.9 (m, 4 H); 13.0 (s, br, 1 H) |
| 15 | 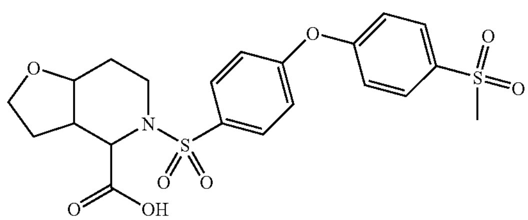 | 481.55 | 481.09 | 1.55-2.1 (4 m, 4 H); 2.5 (m, 1 H); 3.25-3.80 (4 m, 4-5 H, the NMR signal of $H_2O$ overlaps with the signal of the substance); 4.0 (m, 1 H); 4.3 (d, 1 H); 7.3 (m, 4 H); 7.85, 8.0 (2 m, 4 H); 13.0 (s, br, 1 H) |
| 16 | 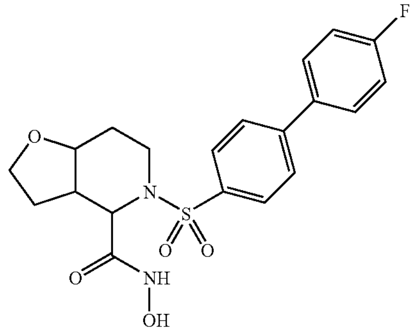 | 420.46 | 421.10 | 1.5-2.0 (3 m, 4 H); 2.4 (m, 1 H); 3.25-3.8 (3 m, 4-5 H, the NMR signal of $H_2O$ overlaps with the signal of the substance); 4.22 (d, 1 H); 7.37 (m, 2 H); 7.85 (m, 6 H); 8.9 (s, 1 H); 10.8 (s, 1 H) |

TABLE 1-continued

| Example | Structure | Molecular weight | ES+ | 1H-NMR |
|---|---|---|---|---|
| 17 | 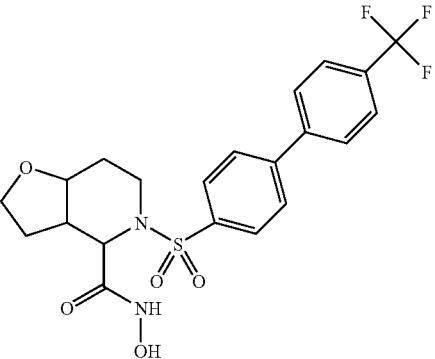 | 470.47 | 471.11 | 1.5-2.0 (3 m, 4 H); 2.4 (m, 1 H); 3.25-3.8 (4 m, 4-5 H, the NMR signal of H₂O overlaps with the signal of the substance); 4.26 (d, 1 H); 7.9 (m, 8 H); 8.9 (s, 1 H); 10.8 (s, 1 H) |
| 18 | 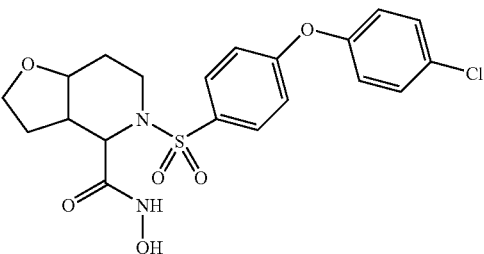 | 452.92 | 452.97 | 1.5-2.0 (3 m, 4 H); 2.4 (m, 1 H); 3.4-3.85 (4 m, 4-5 H, the NMR signal of H₂O overlaps with the signal of the substance); 4.2 (d, 1 H); 7.2 (2 d, 4 H); 7.5; 7.8 (2 d, 4 H), 10.8 (s, 1 H) |
| 19 | 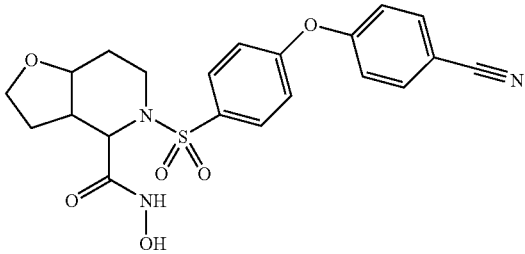 | 443.48 | 444.12 | 1.5-2.0 (3 m, 4 H); 2.4 (m, 1 H); 3.2-3.8 (5 m, 5 H, the NMR signal of H₂O overlaps with the signal of the substance); 4.2 (d, 1 H); 7.3 (m, 4 H); 7.8; 7.9 (2 d, 4 H); 8.9 (s, 1 H); 10.8 (s, 1 H) |
| 20 | 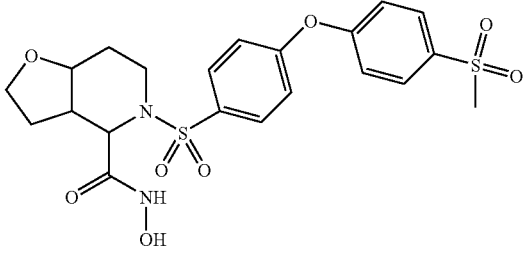 | 496.56 | 497.11 | 1.5-2.0 (4 m, 4 H); 2.4 (m, 1 H); 3.2-3.8 (5 m, 5 H, the NMR signal of H₂O overlaps with the signal of the substance); 4.2 (d, 1 H); 7.3 (2 d, 4 H); 7.85; 8.0 (2 d, 4 H); 8.9 (s, 1 H); 10.8 (s, 1 H) |
| 21 | CHIRAL 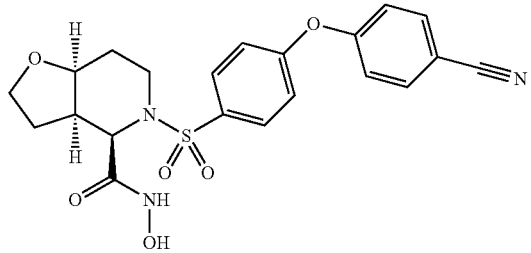 | 443.48 | | from chiral fractionation of Example 19 |

TABLE 1-continued

| Example | Structure | Molecular weight | ES+ | 1H-NMR |
|---|---|---|---|---|
| 22 | CHIRAL | 443.48 | | from chiral fractionation of Example 19 |
| 23 | CHIRAL | 496.56 | | from chiral fractionation of Example 20 |
| 24 | CHIRAL | 496.56 | | from chiral fractionation of Example 20 |

PHARMACOLOGICAL EXAMPLES

Determination of the Enzymatic Activity of the Catalytic Domain of Human Collagenase-1 (MMP-1)

This protein is obtained as inactive proenzyme from Biocol, Potsdam (Catalog No. MMP1). Activation of the proenzyme: 2 parts by volume of proenzyme are incubated with 1 part by volume of APMA solution at 37° C. for 1 hour. The APMA solution is prepared from a 10 mmol/l p-aminophenylmercuric acetate solution in 0.1 mmol/l NaOH by dilution with 3 parts by volume of tris/HCl buffer pH7.5 (see below). The pH is adjusted to between 7.0 and 7.5 by adding 1 mmol/l HCl. After activation of the enzyme, it is diluted with the tris/HCl buffer to a concentration of 2.5 µg/ml.

The enzymic activity is measured by incubating 10 µl of enzyme solution with 10 µl of a 3% strength (v/v) buffered dimethyl sulfoxide solution (reaction 1) for 15 minutes. The enzyme inhibitor activity is measured by incubating 10 µl of enzyme solution with 10 µl of a 3% strength (v/v) buffered dimethyl sulfoxide solution which contains the enzyme inhibitor (reaction 2).

The enzymic reaction both in the case of reaction 1 and in the case of reaction 2 is followed after addition of 10 µl of a 3% strength (v/v) aqueous dimethyl sulfoxide solution which contains 0.3 mmol/l of the substrate by fluorescence spectroscopy (328 nm (extinction)/393 nm (emission)), and the enzymic activity is presented as increase in extinction per minute.

The effect of the inhibitor is calculated as percentage inhibition by the following formula:

% inhibition=100−[(increase in extinction/minute in reaction 2)/(increase in extinction/minute in reaction 1)×100].

The IC50, i.e. the inhibitor concentration necessary for 50% inhibition of the enzymic activity, is determined graphically by plotting the percentage inhibitions at various inhibitor concentrations.

The buffer solution contains 0.05% Brij (Sigma, Deisenhofen, Germany) and 0.1 mol/l tris/HCl, 0.1 mol/l NaCl, 0.01 mol/l CaCl2 (pH=7.5). The enzyme solution contains 2.5 µg/ml of the enzyme domain.

The substrate solution contains 0.3 mmol/l of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-NH2 (Bachem, Heidelberg, Germany).

Preparation and determination of the enzymatic activity of the catalytic domain of human stromelysin (MMP-3) and of neutrophil collagenase (MMP-8). The two enzymes stromelysin (MMP-3) and neutrophil collagenase (MMP-8) were prepared by the method of Ye et al. (Biochemistry; 31 (1992) pages 11 231-11 235). The enzymic activity or the effect of the enzyme inhibitor was measured by incubating 10 µl of enzyme solution with 10 µl of a 3% strength (v/v) buffered dimethyl sulfoxide solution which contained the enzyme inhibitor where appropriate, for 15 minutes. After addition of 10 µl of a 3% strength (v/v) aqueous dimethyl sulfoxide solution which contained 1 mmol/l of the substrate, the enzymic reaction was followed by fluorescence spectroscopy (328 nm (ex)/393 nm(em)).

The enzymic activity is presented as increase in extinction/minute. The IC50 values listed in Table 2 were determined as the inhibitor concentrations leading in each case to 50% inhibition of the enzyme.

The buffer solution contained 0.05% Brij (Sigma, Deisenhofen, Germany) and 0.1 mol/l Tris/HCl, 0.1 mol/l NaCl, 0.01 mol/l CaCl2 and 0.1 mol/l piperazine-N,N'-bis[2-ethanesulfonic acid] (pH=7.5).

The MMP-3 enzyme solution contained 2.3 µg/ml and the MMP-8 enzyme solution 0.6 µg/ml of one of the enzyme domains prepared by the method of Ye et al. The substrate solution contained 1 mmol/l of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-NH2 (Bachem, Heidelberg, Germany).

Determination of the Enzymatic Activity of the Catalytic Domain of Human Collagenase-3 (MMP-13)

This protein was obtained as inactive proenzyme from INVITEK, Berlin (Catalog No. 30 100 803). Activation of the proenzyme: 2 parts by volume of proenzyme were incubated with 1 part by volume of APMA solution at 37° C. for 1.5 hours. The APMA solution was prepared from a 10 mmol/l p-aminophenylmercuric acetate solution in 0.1 mmol/l NaOH by dilution with 3 parts by volume of Tris/HCl buffer pH 7.5 (see below). The pH was adjusted to between 7.0 and 7.5 by adding 1 mmol/l HCl. After activation of the enzyme it was diluted with the Tris/HCl buffer to a concentration of 1.67 µg/ml.

The enzymic activity was measured by incubating 10 µl of enzyme solution with 10 µl of a 3% strength (v/v) buffered dimethyl sulfoxide solution (reaction 1) for 15 minutes. The enzyme inhibitor activity was measured by incubating 10 µl of enzyme solution with 10 µl of a 3% strength (v/v) buffered dimethyl sulfoxide solution which contained the enzyme inhibitor (reaction 2).

The enzymic reaction both in the case of reaction 1 and in the case of reaction 2 was followed after addition of 10 µl of a 3% strength (v/v) aqueous dimethyl sulfoxide solution which contained 0.075 mmol/l of the substrate by fluorescence spectroscopy (328 nm (extinction)/393 nm (emission)).

The enzymic activity has been presented as increase in extinction/minute. The effect of the inhibitor was calculated as percentage inhibition by the following formula:

% inhibition=100−[(increase in extinction/minute in reaction 2)/(increase in extinction/minute in reaction 1)×100].

The IC50, which is the concentration of inhibitor which is necessary for 50% inhibition of the enzymic activity, was determined graphically by plotting the percentage inhibitions at various inhibitor concentrations.

The buffer solution contained 0.05% Brij (Sigma, Deisenhofen, Germany) and 0.1 mol/l Tris/HCl, 0.1 mol/l NaCl, 0.01 mol/l CaCl2 (pH=7.5). The enzyme solution contained 1.67 µg/ml of the enzyme domain. The substrate solution contained 0.075 mmol/l of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-NH2 (Bachem, Heidelberg, Germany).

Determination of the Enzymatic Activity of the Catalytic Domain of Human Gelatinase-A (MMP-2)

This protein was obtained as inactive proenzyme from INVITEK, Berlin (Catalog No. 30 100 602). Activation of the proenzyme: 2 parts by volume of proenzyme were incubated with 1 part by volume of APMA solution at 37° C. for 0.5 hours. The APMA solution was prepared from a 10 mmol/l p-aminophenylmercuric acetate solution in 0.1 mmol/l NaOH by dilution with 3 parts by volume of Tris/HCl buffer pH 7.5 (see below). The pH was adjusted to between 7.0 and 7.5 by adding 1 mmol/l HCl. After activation of the enzyme it was diluted with the Tris/HCl buffer to a concentration of 0.83 µg/ml.

The enzymic activity was measured by incubating 10 µl of enzyme solution with 10 µl of a 3% strength (v/v) buffered dimethyl sulfoxide solution (reaction 1) for 15 minutes. The enzyme inhibitor activity was measured by incubating 10 µl of enzyme solution with 10 µl of a 3% strength (v/v) buffered dimethyl sulfoxide solution which contained the enzyme inhibitor (reaction 2).

The enzymic reaction both in the case of reaction 1 and in the case of reaction 2 was followed after addition of 10 µl of a 3% strength (v/v) aqueous dimethyl sulfoxide solution which contained 0.3 mmol/l of the substrate by fluorescence spectroscopy (328 nm (extinction)/393 nm (emission)).

The enzymic activity has been presented as increase in extinction/minute. The effect of the inhibitor was calculated as percentage inhibition by the following formula:

% inhibition=100−[(increase in extinction/minute in reaction 2)/(increase in extinction/minute in reaction 1)×100].

The IC50, which is the concentration of inhibitor which is necessary for 50% inhibition of the enzymic activity, was determined graphically by plotting the percentage inhibitions at various inhibitor concentrations.

The buffer solution contained 0.05% Brij (Sigma, Deisenhofen, Germany) and 0.1 mol/l Tris/HCl, 0.1 mol/l NaCl, 0.01 mol/l CaCl2 (pH=7.5). The enzyme solution contained 0.83 µg/ml of the enzyme domain. The substrate solution contained 0.3 mmol/l of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-NH2 (Bachem, Heidelberg, Germany).

Determination of the Enzymatic Activity of the Catalytic Domain of Human Gelatinase-A (MMP-9)

This protein was obtained as inactive proenzyme from Roche, Mannheim (Catalog No. 1 758 896). Activation of the proenzyme:

2 parts by volume of proenzyme were incubated with 1 part by volume of APMA solution at 37° C. for 4 hours. The APMA solution was prepared from a 10 mmol/l p-aminophenylmercuric acetate solution in 0.1 mmol/l NaOH by dilution with 3 parts by volume of Tris/HCl buffer pH 7.5 (see below). The pH was adjusted to between 7.0 and 7.5 by adding 1 mmol/l HCl. After activation of the enzyme it was diluted with the Tris/HCl buffer to a concentration of 4.2 mU/ml.

The enzymic activity was measured by incubating 10 µl of enzyme solution with 10 µl of a 3% strength (v/v) buffered dimethyl sulfoxide solution (reaction 1) for 15 minutes. The enzyme inhibitor activity was measured by incubating 10 µl of enzyme solution with 10 µl of a 3% strength (v/v) buffered dimethyl sulfoxide solution which contained the enzyme inhibitor (reaction 2).

The enzymic reaction both in the case of reaction 1 and in the case of reaction 2 was followed after addition of 10 µl of a 3% strength (v/v) aqueous dimethyl sulfoxide solution which contained 0.15 mmol/l of the substrate by fluorescence spectroscopy (328 nm (extinction)/393 nm (emission)).

The enzymic activity has been presented as increase in extinction/minute.

The effect of the inhibitor was calculated as percentage inhibition by the following formula:

% inhibition=100−[(increase in extinction/minute in reaction 2)/(increase in extinction/minute in reaction 1)×100].

The IC50, which is the concentration of inhibitor which is necessary for 50% inhibition of the enzymic activity, was determined graphically by plotting the percentage inhibitions at various inhibitor concentrations.

The buffer solution contained 0.05% Brij (Sigma, Deisenhofen, Germany) and 0.1 mol/l Tris/HCl, 0.1 mol/l NaCl, 0.01 mol/l CaCl2 (pH=7.5). The enzyme solution contained 4.2 mU/ml of the enzyme domain. The substrate solution contained 0.15 mmol/l of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-NH2 (Bachem, Heidelberg, Germany).

Table 2 below shows the results.

TABLE 2

| Example No. | $IC_{50}$ [nM] MMP-1 | $IC_{50}$ [nM] MMP-2 | $IC_{50}$ [nM] MMP-3 | $IC_{50}$ [nM] MMP-8 | $IC_{50}$ [nM] MMP-9 | $IC_{50}$ [nM] MMP-13 |
|---|---|---|---|---|---|---|
| 6 | >10000 | 38 | 3500 | 54 | 2200 | 290 |
| 7 | 29 | 1.7 | 29 | 2.4 | 2.4 | 1.8 |
| 8 | 14 | 0.8 | 13 | 1 | 1.5 | 1 |
| 9 | 4100 | 71 | 1100 | 170 | 120 | 58 |
| 10 | >10000 | 440 | >10000 | 410 | 2500 | 520 |
| 11 | 39 | 2 | 34 | 6 | 3 | 2 |
| 12 | 10 | 0.8 | 14 | 2 | 1.3 | 0.7 |
| 13 | 1400 | 47 | 1500 | 150 | 150 | 63 |

TABLE 2-continued

| Example No. | $IC_{50}$ [nM] MMP-1 | $IC_{50}$ [nM] MMP-2 | $IC_{50}$ [nM] MMP-3 | $IC_{50}$ [nM] MMP-8 | $IC_{50}$ [nM] MMP-9 | $IC_{50}$ [nM] MMP-13 |
|---|---|---|---|---|---|---|
| 18 | 43 | 2 | 27 | 24 | 2 | 1 |
| 21 | 59 | 1 | 17 | 2 | 8 | 1 |
| 23 | 640 | 1 | 15 | 2 | 5 | 1 |

> means greater than.

What is claimed is:

1. A compound identified as follows:
   5-(4'-chlorobiphenyl-4-sulfonyl)octahydrofuro[3,2-c]pyridine-4-carboxylic acid,
   5-(4'-chlorobiphenyl-4-sulfonyl)octahydrofuro[3,2-c]pyridine-4-(N-hydroxy)-carboxamide,
   5-[4-(4-fluorophenoxy)benzenesulfonyl]octahydrofuro[3,2-c]pyridine-4-carboxylic acid,
   5-[4-(4-fluorophenoxy)benzenesulfonyl]octahydrofuro[3,2-c]pyridine-4-(N-hydroxy)-carboxamide,
   5-[4-(4-cyanophenoxy)benzenesulfonyl]octahydrofuro[3,2-c]pyridine-4-carboxylic acid,
   5-[4-(4-methanesulfonylphenoxy)benzenesulfonyl]octahydrofuro[3,2-c]pyridine-4-carboxylic acid,
   5-(4'-fluorobiphenyl-4-sulfonyl)octahydrofuro[3,2-c]pyridine-4-(N-hydroxy)-carboxamide,
   5-(4'-trifluoromethylbiphenyl-4-sulfonyl)octahydrofuro[3,2-c]pyridine-4-(N-hydroxy)-carboxamide,
   5-[4-(4-chlorophenoxy)benzenesulfonyl]octahydrofuro[3,2-c]pyridine-4-(N-hydroxy)-carboxamide,
   5-[4-(4-cyanophenoxy)benzenesulfonyl]octahydrofuro[3,2-c]pyridine-4-(N-hydroxy)-carboxamide or
   5-[4-(4-methanesulfonylphenoxy)benzenesulfonyl]octahydrofuro[3,2-c]pyridine-4-(N-hydroxy)carboxamide.

2. A pharmaceutical composition comprising a pharmaceutically effective amount of one or more compounds of claim 1 together with pharmaceutically suitable and physiologically tolerated carriers, additives or other excipients.

* * * * *